United States Patent
Sugihara

(10) Patent No.: US 10,844,409 B2
(45) Date of Patent: Nov. 24, 2020

(54) METHOD OF PRODUCING LIPID

(71) Applicant: Kao Corporation, Tokyo (JP)

(72) Inventor: Shinji Sugihara, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 16/084,329

(22) PCT Filed: Mar. 31, 2017

(86) PCT No.: PCT/JP2017/013550
§ 371 (c)(1),
(2) Date: Sep. 12, 2018

(87) PCT Pub. No.: WO2017/183421
PCT Pub. Date: Oct. 26, 2017

(65) Prior Publication Data
US 2019/0071698 A1    Mar. 7, 2019

(30) Foreign Application Priority Data

Apr. 20, 2016 (JP) ................. 2016-084680

(51) Int. Cl.
| | | |
|---|---|---|
| C12P 7/64 | (2006.01) | |
| C12P 7/44 | (2006.01) | |
| C12N 9/16 | (2006.01) | |
| C12N 9/10 | (2006.01) | |
| C12N 9/02 | (2006.01) | |
| C12N 9/00 | (2006.01) | |
| C12N 15/82 | (2006.01) | |

(52) U.S. Cl.
CPC .......... *C12P 7/6409* (2013.01); *C12N 9/1029* (2013.01); *C12N 9/16* (2013.01); *C12N 9/93* (2013.01); *C12N 15/8247* (2013.01); *C12P 7/6436* (2013.01); *C12P 7/6454* (2013.01); *C12Y 203/01086* (2013.01); *C12Y 301/02014* (2013.01); *C12Y 602/01* (2013.01)

(58) Field of Classification Search
CPC .... C12N 9/16; C12N 15/8247; C12N 9/1029; C12N 1/12; C12N 9/88; C12P 7/6409; C12P 7/6436; C12P 7/64; C12Y 301/0202
USPC ....... 435/157, 134, 136, 257.2, 252.3, 320.1
See application file for complete search history.

(56) References Cited

U.S. PATENT DOCUMENTS

| | | |
|---|---|---|
| 2003/0017576 A1 | 1/2003 | Aquin et al. |
| 2007/0261138 A1 | 11/2007 | Graham et al. |
| 2013/0102040 A1 | 4/2013 | Radakovits et al. |
| 2013/0344549 A1 | 12/2013 | Roberts et al. |
| 2015/0307860 A1 | 10/2015 | Ozaki et al. |
| 2017/0044580 A1 | 2/2017 | Sugihara et al. |
| 2017/0114376 A1 | 4/2017 | Ozaki et al. |

FOREIGN PATENT DOCUMENTS

| | | |
|---|---|---|
| JP | 2004-534507 A | 11/2004 |
| JP | 2008-514221 A | 5/2008 |
| JP | WO2014/103930 A | 7/2014 |
| JP | WO2015/133305 A | 9/2015 |
| WO | WO 02/040690 A3 | 5/2002 |
| WO | WO 2012/087982 A2 | 6/2012 |

OTHER PUBLICATIONS

Davos et al., Proteins: Structure, Function and Genetics, 2000, vol. 41: 98-107.*
Wristlock et al., Quarterly Reviews of Biophysics 2003, vol. 36 (3): 307-340.*
Kwiatkowski et al., Biochemistry 38:11643-11650, 1999.*
Kisselev L., Structure, 2002, vol. 10: 8-9.*
Excerpted file history, U.S. Appl. No. 15/317,345: Non-final Office action dated Apr. 16, 2019; Reply to restriction requirement filed Mar. 20, 2019; Restriction requirement dated Jan. 30, 2019; Preliminary amendment filed Dec. 8, 2016.
Updated excerpted file history, U.S. Appl. No. 15/317,345: Reply to Non-final Office action filed Jul. 16, 2019, downloaded Sep. 9, 2019 from the United States Patent and Trademark Office, Alexandria, VA.
International Search Report (ISR) for PCT/JP2017/013550; I.A. fd Mar. 31, 2017, dated Jul. 4, 2017 from the Japan Patent Office, Tokyo, Japan.
International Preliminary Report on Patentability (IPRP), Chapter I of the Patent Cooperation Treaty, including the Written Opinion for PCT/JP2017/013550; I.A. fd Mar. 31, 2017, dated Oct. 23, 2018, by the International Bureau of WIPO, Geneva, Switzerland.

(Continued)

*Primary Examiner* — Robert B Mondesi
*Assistant Examiner* — Mohammad Y Meah
(74) *Attorney, Agent, or Firm* — Sterne, Kessler, Goldstein & Fox P.L.L.C.

(57) ABSTRACT

A method of producing lipids, containing the steps of:
culturing a transformant wherein the expressions of a gene encoding any one of the following proteins (A) to (F) and a gene encoding an acyl-ACP thioesterase are enhanced, and
producing fatty acids or lipids containing these fatty acids as components:
(A) a protein consisting of the amino acid sequence set forth in SEQ ID NO: 2;
(B) a protein consisting of an amino acid sequence having 89% or more identity with the amino acid sequence of the protein (A), and having acyl-CoA synthetase activity;
(C) a protein consisting of the amino acid sequence set forth in SEQ ID NO: 4;
(D) a protein consisting of an amino acid sequence having 49% or more identity with the amino acid sequence of the protein (C), and having acyl-CoA synthetase activity;
(E) a protein consisting of the amino acid sequence set forth in SEQ ID NO: 6; and
(F) a protein consisting of an amino acid sequence having 85% or more identity with the amino acid sequence of the protein (E), and having acyl-CoA synthetase activity.

7 Claims, No Drawings
Specification includes a Sequence Listing.

(56) References Cited

OTHER PUBLICATIONS

GenBank: HQ228564.1 [online], Definition: Nannochloropsis oculata long-chain acyl-coenzyme A synthetase (LACS) mRNA, compete cds, Jan. 1, 2012, [retrieved on Jun. 20, 2017] Internet: www.ncbi.nlm.nih.gov/nuccore/HQ228564.

UniProtKB—G9BBC7 (G9BBC7_9STRA) [online], Submitted name: Long-chain acyl-coenzyme A synthetase, Feb. 22, 2012, [retrieved on Jun. 16, 2017], www.uniprot.org/uniprot/G9BBC7.

Agnew, DE et al., "Engineering *Escherichia coli* for production of $C_{12}$-$C_{14}$ polyhydroxyalkanoate from glucose," Metab Eng. Nov. 2012;14(6):705-13. doi: 10.1016/j.ymben.2012.08.003, Academic Press, Orlando, FL.

Hagiwara, H, "Development of sustainable raw materials of fats and oils using microalgae," Bio Industry, vol. 33, Jul. 12, 2016, pp. 41-47.

Tonon, T et al., "Identification of a long-chain polyunsaturated fatty acid acyl-coenzyme A synthetase from the diatom *Thalassiosira pseudonana*," Plant Physiol. May 2005;138(1):402-8. Epub Apr. 8, 2005, American Society of Plant Biologists, Rockville, MD.

Zhang, L et al., "Isolation and characterization of a long-chain acyl-coenzyme A synthetase encoding gene from the marine microalga *Nannochloropsis oculata*," Journal of Applied Phycology, Aug. 2012, vol. 24, Issue 4, pp. 873-880, First Online: Feb. 25, 2012, Springer.

Guo, X et al., "Identification and biochemical characterization of five long-chain acyl-coenzyme A synthetases from the diatom *Phaeodactylum tricornutum*," Plant Physiology and Biochemistry : PPB (Nov. 7, 2013) vol. 74, pp. 33-41, Elsevier Science, Netherlands.

Updated excerpted file history, U.S. Appl. No. 15/317,345, Notice of Allowance and Examiner initiated interview summary, dated Oct. 9, 2019, downloaded Oct. 14, 2019 from the United States Patent and Trademark Office, Alexandria, VA.

\* cited by examiner

SEQUENCE LISTING

<160> NUMBER OF SEQ ID NOS: 62

<210> SEQ ID NO 1
<211> LENGTH: 1947
<212> TYPE: DNA
<213> ORGANISM: Nannochloropsis oculata

<400> SEQUENCE: 1

```
atgcccgcct acacgacgac atcggcgtcc ggggaggtgg acttgcgcat ggagaaggag      60
ggccctggag cttgggagcc ccgaactgtt taccaggtct tcgaggagac tgtccaacgt     120
tacggggacc ggcccgcgct ccacttcaag aaagttccgc acggcggtag ccccgagacg     180
actgagtgga gcgtttacac atggcgcgaa tactatgacc tgaccctcac cttcgccaag     240
agcctcctgg ccctcgactt cccggcccac ggggccatca acatcatcgg tttcaactcg     300
cctgagtggc tcatcgccaa ctgcggtgcc attgccgcg tggcgtggg tgtgggtatc      360 tatacgagca acaacgcgga ggcctgcaat tacatctcgg agcactcgga ggctgaagtg     420
gttgtggtgg agaacgctaa gcagctggag aagtacgtaa aaatcgccaa gaacctgccc     480
cgccttaagg cgctggtggt gtacgatggc acgggcgagg gattcacgtg tgacacgcct     540
atatactcct ggaaggcctt catggcactg ggaaaggaca aaagcgaggc agcggtccgt     600
gcgcgcattg aggcccagcg gcccggacat tgttgcacgc tcatctacac gtccggcacc     660
acgggcccgc ccaaggccgt catgtatatcg cacgataacc tgacctggac cgtcaaaaac     720
tttgtggctg ccctgccttt cacgcttact tgcgaggacc ggtcggtgtc ctccctgccg     780
ctgtcccacg tggcggcaca gatgctggac gtgcactgcc ccatcgcctc gggcgctaag     840
atttatttcg cgcaggccga cgcactccgg ggctcgctac ccaacacgct gaaggatgtc     900
tgtcccacct acttttttgg cgtaccgcgt gtctgggaga agatctacga gaaaatgcag     960
gaggtggcgc gctccaccac aggggtcaag cgggcgctgg cccagtgggc caaagccaag    1020
ggattggaga agaaccggcg ccagcaatat ggggggcggtg gtggggcgcc cgtgggattc    1080
ggttgcgctt acgccctcgt cctgtccaaa gtgaaggcg cgctagggct gcaccagacc    1140
aagatctgca tcacctcggc agcgcccata tccgtcgagg tgctcgaata cttcgcctcc    1200
ctggacatcc ctgtgctaga gctgttcggg cagtccgagt gcacaggccc acacacctcc    1260
aacttctcct acgcctggaa gatcggctcc attggccgcg acataccggg ggttaagacc    1320
aaacaggaag cggccgccaa ggaattctgc atgttcgggc ggcacattat gatgggctac    1380
atgaagatgg aggagaagac caaggaggca gtggacgagg agggttggct gcattcagga    1440
gacgtggccg acgtggatgc ggacgggttc tggaccatca cggccgtat caaggagctc    1500 atcatcacgg ccggcgggga gaacatcccg cccgtgctaa ttgagaccga ggtcaaggcc    1560
gcccttcacg ccgtggctaa ttgcatggtg gtgggcgata agaagaaatt tttgactgtg    1620
ctgctgacga tgaagaccaa gctggacgag cagggcaacc ccacgaacgc cttgaaccgc    1680
gaggccctgg atatcggaa agagctgggc tcggaagcca caaccacgga gcaggtcggc    1740
```

-continued

```
aaggaccctg cctggaagaa gtatttcgac gaggggctca agaaggccaa tgccgccgcc    1800
acctctaatg cgcagttcgt acagaagtgg gccgtgctgc ccttggactt ctccgagaag    1860
ggcggcgagc tcacgcccac gctcaagctc aaacgctctg tggtggccga aaatacgcc    1920 gacgtcatcg ccaatctcta caagtag                                        1947

<210> SEQ ID NO 2
<211> LENGTH: 648
<212> TYPE: PRT
<213> ORGANISM: Nannochloropsis oculata

<400> SEQUENCE: 2

Met Pro Ala Tyr Thr Thr Ser Ala Ser Gly Glu Val Asp Leu Arg
1               5                   10                  15

Met Glu Lys Glu Gly Pro Gly Ala Trp Glu Pro Arg Thr Val Tyr Gln
                20                  25                  30

Val Phe Glu Glu Thr Val Gln Arg Tyr Gly Asp Arg Pro Ala Leu His
            35                  40                  45

Phe Lys Lys Val Pro His Gly Gly Ser Pro Glu Thr Thr Glu Trp Ser
        50                  55                  60

Val Tyr Thr Trp Arg Glu Tyr Tyr Asp Leu Thr Leu Thr Phe Ala Lys
65                  70                  75                  80

Ser Leu Leu Ala Leu Asp Phe Pro Ala His Gly Ala Ile Asn Ile Ile
                85                  90                  95

Gly Phe Asn Ser Pro Glu Trp Leu Ile Ala Asn Cys Gly Ala Ile Ala
            100                 105                 110

Ala Gly Gly Val Gly Val Gly Ile Tyr Thr Ser Asn Asn Ala Glu Ala
        115                 120                 125

Cys Asn Tyr Ile Ser Glu His Ser Glu Ala Glu Val Val Val Val Glu
    130                 135                 140

Asn Ala Lys Gln Leu Glu Lys Tyr Val Lys Ile Ala Lys Asn Leu Pro
145                 150                 155                 160

Arg Leu Lys Ala Leu Val Val Tyr Asp Gly Thr Gly Glu Gly Phe Thr
                165                 170                 175

Cys Asp Thr Pro Ile Tyr Ser Trp Lys Ala Phe Met Ala Leu Gly Lys
            180                 185                 190

Asp Lys Ser Glu Ala Ala Val Arg Ala Arg Ile Glu Ala Gln Arg Pro
        195                 200                 205

Gly His Cys Cys Thr Leu Ile Tyr Thr Ser Gly Thr Thr Gly Pro Pro
    210                 215                 220

Lys Ala Val Met Ile Ser His Asp Asn Leu Thr Trp Thr Val Lys Asn
225                 230                 235                 240

Phe Val Ala Ala Leu Pro Phe Thr Leu Thr Cys Glu Asp Arg Ser Val
                245                 250                 255

Ser Ser Leu Pro Leu Ser His Val Ala Ala Gln Met Leu Asp Val His
            260                 265                 270

Cys Pro Ile Ala Ser Gly Ala Lys Ile Tyr Phe Ala Gln Ala Asp Ala
        275                 280                 285

Leu Arg Gly Ser Leu Pro Asn Thr Leu Lys Asp Val Cys Pro Thr Tyr
    290                 295                 300

Phe Phe Gly Val Pro Arg Val Trp Glu Lys Ile Tyr Glu Lys Met Gln
305                 310                 315                 320

Glu Val Ala Arg Ser Thr Thr Gly Val Lys Arg Ala Leu Ala Gln Trp
                325                 330                 335
```

Ala Lys Ala Lys Gly Leu Glu Lys Asn Arg Arg Gln Gln Tyr Gly Gly
            340                 345                 350

Gly Gly Gly Ala Pro Val Gly Phe Gly Cys Ala Tyr Ala Leu Val Leu
            355                 360                 365

Ser Lys Val Lys Ala Ala Leu Gly Leu His Gln Thr Lys Ile Cys Ile
370                 375                 380

Thr Ser Ala Ala Pro Ile Ser Val Glu Val Leu Glu Tyr Phe Ala Ser
385                 390                 395                 400

Leu Asp Ile Pro Val Leu Glu Leu Phe Gly Gln Ser Glu Cys Thr Gly
                405                 410                 415

Pro His Thr Ser Asn Phe Ser Tyr Ala Trp Lys Ile Gly Ser Ile Gly
                420                 425                 430

Arg Asp Ile Pro Gly Val Lys Thr Lys Gln Glu Ala Ala Ala Lys Glu
            435                 440                 445

Phe Cys Met Phe Gly Arg His Ile Met Met Gly Tyr Met Lys Met Glu
450                 455                 460

Glu Lys Thr Lys Glu Ala Val Asp Glu Glu Gly Trp Leu His Ser Gly
465                 470                 475                 480

Asp Val Ala Asp Val Asp Ala Asp Gly Phe Trp Thr Ile Thr Gly Arg
                485                 490                 495

Ile Lys Glu Leu Ile Ile Thr Ala Gly Gly Glu Asn Ile Pro Pro Val
            500                 505                 510

Leu Ile Glu Thr Glu Val Lys Ala Ala Leu His Ala Val Ala Asn Cys
            515                 520                 525

Met Val Val Gly Asp Lys Lys Phe Leu Thr Val Leu Leu Thr Met
530                 535                 540

Lys Thr Lys Leu Asp Glu Gln Gly Asn Pro Thr Asn Ala Leu Asn Arg
545                 550                 555                 560

Glu Ala Leu Asp Ile Gly Lys Glu Leu Gly Ser Glu Ala Thr Thr Thr
                565                 570                 575

Glu Gln Val Gly Lys Asp Pro Ala Trp Lys Lys Tyr Phe Asp Glu Gly
            580                 585                 590

Leu Lys Lys Ala Asn Ala Ala Ala Thr Ser Asn Ala Gln Phe Val Gln
            595                 600                 605

Lys Trp Ala Val Leu Pro Leu Asp Phe Ser Glu Lys Gly Gly Glu Leu
610                 615                 620

Thr Pro Thr Leu Lys Leu Lys Arg Ser Val Val Ala Glu Lys Tyr Ala
625                 630                 635                 640

Asp Val Ile Ala Asn Leu Tyr Lys
                645

<210> SEQ ID NO 3
<211> LENGTH: 3189
<212> TYPE: DNA
<213> ORGANISM: Nannochloropsis oculata

<400> SEQUENCE: 3
atggcgctct tggccaggtg gaaggacgta gtaaagagca aaccagacgc cccagccttg    60
atactctcgg acggcctctc ctccagatcc tccaatacta caccagcttt cgagacttg    120 gaccgctcca gcgatgccct gctgcattc ctgtcggtgg caggactgtt gcctttcgac    180
agggttggca tttgctttca tccgtcacag ccggccgaga tagtttccct cctagcgctg    240
ctgaaatgtg aggctatcgc agtgccaatg cgccggccat ttctcaacga gattgtgacc    300

```
gacgctgggt tgcgtctagc attagtccct cgttgtgaca acaaggaggc agcgtcttta    360
actgcctttc ttcaagtcct gcggttgggg ccgcgcggag aggtggacac cgacgatgct    420
gctggccttg cgccattgcc tcctccccaa ccccctcgct ccagcctgat aggtgccatc    480
aatatacttt atacctcggg cagtactggg cgacccaaag gagtgattgg tcgggagagc    540
ggattttttt atcgcatccg ctggatgcat caggcatttc catttgtcga gggccatgaa    600
gaggttgtgt tgcggcggac gcctctcact tttgtggact cgatgtggga gatctggggc    660
gcacttttag ggggtgtacc gttgtttctc cacacggctg ccttgggtaa gaaacaagat    720
cccgccttct tggcttgccc gggagcgact cgggcgacac tcacgccctc cttgctcgcg    780
gctttgctcc aatgtaacgc accgattttg agagctggga gttcgctacg cacctgcctt    840
tgtagtgggg aggctctgtc ttgggatttg gcgaagcaat ttctggctcg ttcgccgtca    900
tgcaccctac ttcatctcta tggctccacg gaggtctcag gagacgcaag ctgggccgca    960
cttacgacga aggcgacaga aatagggggac gaaaaggaat tacagccaac acccggcctt   1020
gtcccgctgg gaagagccat tcccggcacg tatctatgga tagtagagga caggacgggg   1080
gaaaagattc aaattggaga aggaagcgta ggcgcagttg acatagatgg ggagctatgg    1140
gtggcaggac ctggagtagc gctgggctat tacggatatc ctcccgagag tgacctcgat    1200
tcgaaattcg gacgattgag tgtgaggaat tcctcttttgt tgcttttttaa gacggggat    1260
tgggtgcgtt atgtttcaga aggctccaac cagaaggatg gaagtgagaa aggacaacgg   1320
cacacgctcc tttatcgtgg ccggcgaggt gacagctttg tcaaggtcag gggagtacgc    1380
atgggcttgg aggaggccga gcagcggacg gcgtcggcgc ttggttttga agtaagtggt    1440
gggaatctgg gcatgatggt ggtacagggt cgaagcatat ctgccagaga agatgccgta    1500
ctgttgctgg cattgacgtg ggaggtggcc acgcgctgga cagacgctgc cgagcttcga    1560
aaatgtctgc ggactgcggg actgccagct gagatgatac cgtctcagat tattgtgggc    1620
gtcaaaggtc aaccccctgcc gctaacctcg agcggaaaga tggacagaca acagctcgct   1680
tgttgggggtt cggagtttct cgtacgagga acaccgatgg ggcagctggc aaaagaagag   1740
gacgacatag agaaatggct cgaggactgc tttgcaaagt tggttgggag gcagcattct    1800
gaggggcaaa gggggcttag cctgtttgac cgagggggggc attcattgat gatgatgcaa   1860
gctttgagcg agattgagac acgttttggg aaggccagtg caggattgat ggtgcacgac    1920
ttggcgagga ctgtgccgga gattgccaga ttgctgtcgc aaacacagca cccagggaat    1980
gtaaagaaac ggatgagaag tcatgaggag aataacagcg acatatccca ggggctacga    2040
cttatgaatc gctggcgctt tgctttcgag aagtgtgtgg atgcaccgcc ttgcttggtt    2100
ttgatagggc cgatggaggt atggtgggtg ttggtcggcg cgcatgatca tttcttcgta    2160
gctcttgact tgaagaccgg taaggagcag tggcggaccc gtgtagaggg tcgtatcgag    2220
ggagaagcag cggtgcaagg gcctctcgtc ttcgtaccct cccatgactc ccggctgtat    2280
gcattttcaa tcaggaccgg gaagctggca tggtcatatc gcacggaggg agaaatcaag    2340
agcgctcctt tacccttctg ccttgccggc ccagcagata ccaaagatat caagttagtc    2400
ggctttggca gctacgacgg tcatctttat atcgtcaagg catcttctgg agagttgtgg    2460
gccccaccta gctcgctcgg cgggagtccg tttgcctctc cgcttcttct gccagcagca    2520
gcagcagggg cagcccgact ggtcacagtc accaaccgtg ggcgtgtcgc tcagtggctt    2580
gtgcaaggac aagggacagt gacacttgat tggtgtcaag aagtggggttg cgcggtcttc    2640
acgacgccca tcttctctcg cgcctcatcc cttcttgtcc ttggcggcac ggacgggtct    2700
```

-continued

```
gctttggctt tggacccagc ccaaggtgga agactggtgt ggcgggtgat gctaaatgga    2760
tctgacggcg taagtgccgc acctgtcttt gcctccccat gtctactacc tgctaatgac    2820
gaggatgacg aaggtgtgct ggtagcctgt gaaagctccc tccactgcct ggtaattaca    2880
agtggaaagc ggaaatggct catcgatacg tcagcaaggg agggcgaggt cattaccggg    2940
aagccggtag tgctgaatgg cagtcgtttt gtcttggttg gcacatctca gggcaggata    3000
attgtttgga gtgcgcaaaa aaagcggcct gaacatgtgg cgacgttaaa tatgggcctt    3060
ggccggcgtt taagcagccc caccgtcgtg ttggcctcga aaagattggt ggatgacaag    3120
aacagctgga ttactgtggt gggctcgcgc gacgagggtg tgtatatggt ggaaatagag    3180
gagatgtaa                                                             3189
```

<210> SEQ ID NO 4
<211> LENGTH: 1062
<212> TYPE: PRT
<213> ORGANISM: Nannochloropsis oculata

<400> SEQUENCE: 4

```
Met Ala Leu Leu Ala Arg Trp Lys Asp Val Val Lys Ser Lys Pro Asp
 1               5                  10                  15

Ala Pro Ala Leu Ile Leu Ser Asp Gly Leu Ser Ser Arg Ser Ser Asn
             20                  25                  30

Thr Asn Thr Ser Phe Arg Asp Leu Asp Arg Ser Ser Asp Ala Leu Ala
         35                  40                  45

Ala Phe Leu Ser Val Ala Gly Leu Leu Pro Phe Asp Arg Val Gly Ile
     50                  55                  60

Cys Phe His Pro Ser Gln Pro Ala Glu Ile Val Ser Leu Leu Ala Leu
 65                  70                  75                  80

Leu Lys Cys Glu Ala Ile Ala Val Pro Met Arg Arg Pro Phe Leu Asn
                 85                  90                  95

Glu Ile Val Thr Asp Ala Gly Leu Arg Leu Ala Leu Val Pro Arg Cys
            100                 105                 110

Asp Asn Lys Glu Ala Ala Ser Leu Thr Ala Phe Leu Gln Val Leu Arg
        115                 120                 125

Leu Gly Pro Arg Gly Glu Val Asp Thr Asp Ala Ala Gly Leu Ala
    130                 135                 140

Pro Leu Pro Pro Pro Gln Pro Pro Arg Ser Ser Leu Ile Gly Ala Ile
145                 150                 155                 160

Asn Ile Leu Tyr Thr Ser Gly Ser Thr Gly Arg Pro Lys Gly Val Ile
                165                 170                 175

Gly Arg Glu Ser Gly Phe Phe Tyr Arg Ile Arg Trp Met His Gln Ala
            180                 185                 190

Phe Pro Phe Val Glu Gly His Glu Glu Val Val Leu Arg Arg Thr Pro
        195                 200                 205

Leu Thr Phe Val Asp Ser Met Trp Glu Ile Trp Gly Ala Leu Leu Gly
    210                 215                 220

Gly Val Pro Leu Phe Leu His Thr Ala Ala Leu Gly Lys Lys Gln Asp
225                 230                 235                 240

Pro Ala Phe Leu Ala Cys Pro Gly Ala Thr Arg Ala Thr Leu Thr Pro
                245                 250                 255

Ser Leu Leu Ala Ala Leu Leu Gln Cys Asn Ala Pro Ile Leu Arg Ala
            260                 265                 270

Gly Ser Ser Leu Arg Thr Cys Leu Cys Ser Gly Glu Ala Leu Ser Trp
```

```
                275                 280                 285
Asp Leu Ala Lys Gln Phe Leu Ala Arg Ser Pro Ser Cys Thr Leu Leu
            290                 295                 300
His Leu Tyr Gly Ser Thr Glu Val Ser Gly Asp Ala Ser Trp Ala Ala
305                 310                 315                 320
Leu Thr Thr Lys Ala Thr Glu Ile Gly Asp Lys Glu Leu Gln Pro
            325                 330                 335
Thr Pro Gly Leu Val Pro Leu Gly Arg Ala Ile Pro Gly Thr Tyr Leu
            340                 345                 350
Trp Ile Val Glu Asp Arg Thr Gly Glu Lys Ile Gln Ile Gly Glu Gly
            355                 360                 365
Ser Val Gly Ala Val Asp Ile Asp Gly Glu Leu Trp Val Ala Gly Pro
        370                 375                 380
Gly Val Ala Leu Gly Tyr Tyr Gly Tyr Pro Pro Glu Ser Asp Leu Asp
385                 390                 395                 400
Ser Lys Phe Gly Arg Leu Ser Val Arg Asn Ser Ser Leu Leu Leu Phe
                405                 410                 415
Lys Thr Gly Asp Trp Val Arg Tyr Val Ser Glu Gly Ser Asn Gln Lys
            420                 425                 430
Asp Gly Ser Glu Lys Gly Gln Arg His Thr Leu Leu Tyr Arg Gly Arg
        435                 440                 445
Arg Gly Asp Ser Phe Val Lys Val Arg Gly Val Arg Met Gly Leu Glu
        450                 455                 460
Glu Ala Glu Gln Arg Thr Ala Ser Ala Leu Gly Leu Glu Val Ser Gly
465                 470                 475                 480
Gly Asn Leu Gly Met Met Val Val Gln Gly Arg Ser Ile Ser Ala Arg
                485                 490                 495
Glu Asp Ala Val Leu Leu Leu Ala Leu Thr Trp Glu Val Ala Thr Arg
                500                 505                 510
Trp Thr Asp Ala Ala Glu Leu Arg Lys Cys Leu Arg Thr Ala Gly Leu
            515                 520                 525
Pro Ala Glu Met Ile Pro Ser Gln Ile Ile Val Gly Val Lys Gly Gln
        530                 535                 540
Pro Leu Pro Leu Thr Ser Ser Gly Lys Met Asp Arg Gln Gln Leu Ala
545                 550                 555                 560
Cys Trp Gly Ser Glu Phe Leu Val Arg Gly Thr Pro Met Gly Gln Leu
                565                 570                 575
Ala Lys Glu Glu Asp Asp Ile Glu Lys Trp Leu Glu Asp Cys Phe Ala
            580                 585                 590
Lys Leu Val Gly Arg Gln His Ser Glu Gly Gln Arg Gly Leu Ser Leu
            595                 600                 605
Phe Asp Arg Gly Gly His Ser Leu Met Met Met Gln Ala Leu Ser Glu
        610                 615                 620
Ile Glu Thr Arg Phe Gly Lys Ala Ser Ala Gly Leu Met Val His Asp
625                 630                 635                 640
Leu Ala Arg Thr Val Pro Glu Ile Ala Arg Leu Leu Ser Gln Thr Gln
                645                 650                 655
His Pro Gly Asn Val Lys Lys Arg Met Arg Ser His Glu Glu Asn Asn
            660                 665                 670
Ser Asp Ile Ser Gln Gly Leu Arg Leu Met Asn Arg Trp Arg Phe Ala
            675                 680                 685
Phe Glu Lys Cys Val Asp Ala Pro Pro Cys Leu Val Leu Ile Gly Pro
        690                 695                 700
```

Met Glu Val Trp Trp Val Leu Val Gly Ala His Asp His Phe Val
705                 710                 715                 720

Ala Leu Asp Leu Lys Thr Gly Lys Glu Gln Trp Arg Thr Arg Val Glu
            725                 730                 735

Gly Arg Ile Glu Gly Glu Ala Ala Val Gln Gly Pro Leu Val Phe Val
                740                 745                 750

Pro Ser His Asp Ser Arg Leu Tyr Ala Phe Ser Ile Arg Thr Gly Lys
            755                 760                 765

Leu Ala Trp Ser Tyr Arg Thr Glu Gly Glu Ile Lys Ser Ala Pro Leu
        770                 775                 780

Pro Phe Cys Leu Ala Gly Pro Ala Asp Thr Lys Asp Ile Lys Leu Val
785                 790                 795                 800

Gly Phe Gly Ser Tyr Asp Gly His Leu Tyr Ile Val Lys Ala Ser Ser
                805                 810                 815

Gly Glu Leu Trp Ala Pro Pro Ser Ser Leu Gly Gly Ser Pro Phe Ala
            820                 825                 830

Ser Pro Leu Leu Leu Pro Ala Ala Ala Gly Ala Ala Arg Leu Val
        835                 840                 845

Thr Val Thr Asn Arg Gly Arg Val Ala Gln Trp Leu Val Gln Gly Gln
    850                 855                 860

Gly Thr Val Thr Leu Asp Trp Cys Gln Glu Val Gly Cys Ala Val Phe
865                 870                 875                 880

Thr Thr Pro Ile Phe Ser Arg Ala Ser Ser Leu Leu Val Leu Gly Gly
                885                 890                 895

Thr Asp Gly Ser Ala Leu Ala Leu Asp Pro Ala Gln Gly Gly Arg Leu
            900                 905                 910

Val Trp Arg Val Met Leu Asn Gly Ser Asp Gly Val Ser Ala Ala Pro
        915                 920                 925

Val Phe Ala Ser Pro Cys Leu Leu Pro Ala Asn Asp Glu Asp Glu
930                 935                 940

Gly Val Leu Val Ala Cys Glu Ser Ser Leu His Cys Leu Val Ile Thr
945                 950                 955                 960

Ser Gly Lys Arg Lys Trp Leu Ile Asp Thr Ser Ala Arg Glu Gly Glu
                965                 970                 975

Val Ile Thr Gly Lys Pro Val Val Leu Asn Gly Ser Arg Phe Val Leu
            980                 985                 990

Val Gly Thr Ser Gln Gly Arg Ile Ile Val Trp Ser Ala Gln Lys Lys
        995                 1000                1005

Arg Pro Glu His Val Ala Thr Leu Asn Met Gly Leu Gly Arg Arg
    1010                1015                1020

Leu Ser Ser Pro Thr Val Val Leu Ala Ser Lys Arg Leu Val Asp
    1025                1030                1035

Asp Lys Asn Ser Trp Ile Thr Val Val Gly Ser Arg Asp Glu Gly
    1040                1045                1050

Val Tyr Met Val Glu Ile Glu Glu Met
    1055                1060

<210> SEQ ID NO 5
<211> LENGTH: 2247
<212> TYPE: DNA
<213> ORGANISM: Nannochloropsis oculata

<400> SEQUENCE: 5
atgggcaata caccctccga ttcctcttcc tcctccaaga cgggcgtgga aaaggattgt    60

-continued

```
agccagcagt acgctaacac cagtccgagc tcccggtcgc cttccccgcg ggtaggcaaa    120
agtaagctca tcgaggggc ccttttagtc tcccacggcg gcagcagcaa tagcagccca    180
agcagcagca gcagcagcaa cagcagcagc aacagcagca gcagcagccc gagaaggagc    240
agcagcggca gtatgagcaa gtcaggagag gaaaaggctg tgtatgccat cacgacggct    300
gaagaggtgc caccgcgcat cctggcttcg gctaaggacg ggccgggcga tgtggcgccc    360
attacgctct accagtcctt cgaggcggcg gtggctaatt ggggagaccg ccctcgctg    420 ggggtgaaac gaccagggcc gggccaagct ctgaaggaca ccccttctc cttctacacc    480 tggagggagt acttcgcggt ctcccagcgt ttcggccggg ccttgatggc ccttggcttc    540
cagccgcacg gcgtcatcaa catcctgggc ttcaatgcgc ccgagtggtt cttctcctac    600
atgggcgcga tgatggccgg cggggtggct gccggcattt acatcaccaa cggcccggag    660
gcctgtcact acatcacgaa gcactcggat gcggagatgg tggtggtgga cgacgtcagc    720
cagctcaaga aatacgccac ggctaccaaa gaccagcttc ccagacttaa ggccatgatt    780
ctctacggcg gacaagccct ccccaccgac cttaaatttg cccacccggg gattaaactc    840
tacaccttcg acgacttcct caagctggcc gagggcgtgc cggagacgca gatccgcgcc    900
cgcgccgagg ctatgcgtcc cggccactgc gtcacgctca tctacacctc cggcaccacc    960 ggcccctccca aggccgtgat gctctcgcac gacaacctga cgtgggtcgg cgctatggtt    1020
gcttatcact tcaccgaccg ccggcccacg gacaggctcg tctcctacct gcccttgagc    1080
cacatcgcgg cgcagataat cgacattctg gtgcccttcg gctgtggcgg ttgcgtctat    1140
ttcgcccagc cggatgccct aagggggtcg ctcgtgcaca ccctccggga agtccgcccg    1200
caggtcttct tcgccgtccc tcgtgtatgg gagaagatgt acgaggccat gcagcaggcc    1260
cgcaaagccg ccccctctccc cctccgcctg ctctcggaca ccctcaagaa gagcatgaag    1320
acccacgtcc tctccacgca atacgggcac gacgtcatcc gccccgccct cctcccctg    1380 gccaacaaga tgttcgacaa ggttaaggag aagctgggcc tggacgaggg ccgctactgc    1440
gctacgggcg ctgcaccact ctcccccgag atccaggcct atttcgcctc catcggcatc    1500
accgtcttcg aggtcttcgg acagagcgag gcgacgggtc tgaccacttg caactgccct    1560
caggcttgga agctcggaac ggtcggccgg atttatccgg ccaagaatg ccaggccgac    1620 ccggcatcgg gcgagttcca gtaccgcggt cgccacgtct ttatgggcta cctccacaac    1680
ctcgaggaga ccaagcaagc cctccttccc ggcggctggc tgcgttcggg cgacgtcgcc    1740
tccatcgacg ccgaccacga gcccaacacg cccaagccca gcggctttgt ccgtatcacg    1800
ggcaggatca aggagcttat catcacggca ggcggtgaaa acattcctcc cgtcctcatc    1860
gagaacgaac tcaaggccgc cctgcccgcc cttgcctcct gcatggtcgt cggggaccag    1920
aagaagtacc tgaccgtcct cctgacggtg cacttgacgg aggaagggaa gctcacaggc    1980
ccctccctcg aggcgggcca agccctcggc agtcaggctg acactcccgc gccgtccgt    2040 gccgatcctc tctggcaaga ttacttcaat gccggtctca agacggccaa cagcaaggcc    2100
acgagccgcg ctcagttcgt ccaacggtac gccgtcctgg acaaggaatt cagcgaaaag    2160 gacgggatt tgactcccac cctcaagctc aaacgcagcg tggtggccaa gaagcaagcg    2220
gcgctgatcg agtctctgta caaatga                                        2247
```

<210> SEQ ID NO 6
<211> LENGTH: 748
<212> TYPE: PRT

-continued

<213> ORGANISM: Nannochloropsis oculata

<400> SEQUENCE: 6

```
Met Gly Asn Thr Pro Ser Asp Ser Ser Ser Ser Lys Thr Gly Val
 1               5                  10                  15

Glu Lys Asp Cys Ser Gln Gln Tyr Ala Asn Thr Ser Pro Ser Arg
            20                  25                  30

Ser Pro Ser Pro Arg Val Gly Lys Ser Lys Leu Ile Glu Gly Ala Leu
        35                  40                  45

Leu Val Ser His Gly Gly Ser Ser Asn Ser Ser Pro Ser Ser Ser
        50                  55                  60

Ser Ser Asn Ser Ser Asn Ser Ser Ser Ser Pro Arg Arg Ser
 65                  70                  75                  80

Ser Ser Gly Ser Met Ser Lys Ser Gly Glu Glu Lys Ala Val Tyr Ala
                85                  90                  95

Ile Thr Thr Ala Glu Glu Val Pro Pro Arg Ile Leu Ala Ser Ala Lys
                100                 105                 110

Asp Gly Pro Gly Asp Val Ala Pro Ile Thr Leu Tyr Gln Ser Phe Glu
            115                 120                 125

Ala Ala Val Ala Asn Trp Gly Asp Arg Pro Ser Leu Gly Val Lys Arg
    130                 135                 140

Pro Gly Pro Gly Gln Ala Leu Lys Asp Thr Pro Phe Ser Phe Tyr Thr
145                 150                 155                 160

Trp Arg Glu Tyr Phe Ala Val Ser Gln Arg Phe Gly Arg Ala Leu Met
                165                 170                 175

Ala Leu Gly Phe Gln Pro His Gly Val Ile Asn Ile Leu Gly Phe Asn
            180                 185                 190

Ala Pro Glu Trp Phe Phe Ser Tyr Met Gly Ala Met Met Ala Gly Gly
    195                 200                 205

Val Ala Ala Gly Ile Tyr Ile Thr Asn Gly Pro Glu Ala Cys His Tyr
210                 215                 220

Ile Thr Lys His Ser Asp Ala Glu Met Val Val Asp Asp Val Ser
225                 230                 235                 240

Gln Leu Lys Lys Tyr Ala Thr Ala Thr Lys Asp Gln Leu Pro Arg Leu
                245                 250                 255

Lys Ala Met Ile Leu Tyr Gly Gly Gln Ala Leu Pro Thr Asp Leu Lys
            260                 265                 270

Phe Ala His Pro Gly Ile Lys Leu Tyr Thr Phe Asp Asp Phe Leu Lys
    275                 280                 285

Leu Ala Glu Gly Val Pro Glu Thr Gln Ile Arg Ala Arg Ala Glu Ala
290                 295                 300

Met Arg Pro Gly His Cys Val Thr Leu Ile Tyr Thr Ser Gly Thr Thr
305                 310                 315                 320

Gly Pro Pro Lys Ala Val Met Leu Ser His Asp Asn Leu Thr Trp Val
                325                 330                 335

Gly Ala Met Val Ala Tyr His Phe Thr Asp Arg Arg Pro Thr Asp Arg
            340                 345                 350

Leu Val Ser Tyr Leu Pro Leu Ser His Ile Ala Ala Gln Ile Ile Asp
    355                 360                 365

Ile Leu Val Pro Phe Gly Cys Gly Gly Cys Val Tyr Phe Ala Gln Pro
370                 375                 380

Asp Ala Leu Arg Gly Ser Leu Val His Thr Leu Arg Glu Val Arg Pro
385                 390                 395                 400
```

Gln Val Phe Phe Ala Val Pro Arg Val Trp Glu Lys Met Tyr Glu Ala
                405                 410                 415
Met Gln Gln Ala Arg Lys Ala Ala Pro Leu Pro Leu Arg Leu Leu Ser
            420                 425                 430
Asp Thr Leu Lys Lys Ser Met Lys Thr His Val Leu Ser Thr Gln Tyr
        435                 440                 445
Gly His Asp Val Ile Arg Pro Ala Leu Leu Pro Leu Ala Asn Lys Met
    450                 455                 460
Phe Asp Lys Val Lys Glu Lys Leu Gly Leu Asp Glu Gly Arg Tyr Cys
465                 470                 475                 480
Ala Thr Gly Ala Ala Pro Leu Ser Pro Glu Ile Gln Ala Tyr Phe Ala
                485                 490                 495
Ser Ile Gly Ile Thr Val Phe Glu Val Phe Gly Gln Ser Glu Ala Thr
            500                 505                 510
Gly Leu Thr Thr Cys Asn Cys Pro Gln Ala Trp Lys Leu Gly Thr Val
        515                 520                 525
Gly Arg Ile Tyr Pro Gly Gln Glu Cys Gln Ala Asp Pro Ala Ser Gly
    530                 535                 540
Glu Phe Gln Tyr Arg Gly Arg His Val Phe Met Gly Tyr Leu His Asn
545                 550                 555                 560
Leu Glu Glu Thr Lys Gln Ala Leu Leu Pro Gly Gly Trp Leu Arg Ser
                565                 570                 575
Gly Asp Val Ala Ser Ile Asp Ala Asp His Glu Pro Asn Thr Pro Lys
            580                 585                 590
Pro Ser Gly Phe Val Arg Ile Thr Gly Arg Ile Lys Glu Leu Ile Ile
        595                 600                 605
Thr Ala Gly Gly Glu Asn Ile Pro Pro Val Leu Ile Glu Asn Glu Leu
    610                 615                 620
Lys Ala Ala Leu Pro Ala Leu Ala Ser Cys Met Val Val Gly Asp Gln
625                 630                 635                 640
Lys Lys Tyr Leu Thr Val Leu Leu Thr Val His Leu Thr Glu Glu Gly
                645                 650                 655
Lys Leu Thr Gly Pro Ser Leu Glu Ala Gly Gln Ala Leu Gly Ser Gln
            660                 665                 670
Ala Asp Thr Pro Ala Ala Val Arg Ala Asp Pro Leu Trp Gln Asp Tyr
        675                 680                 685
Phe Asn Ala Gly Leu Lys Thr Ala Asn Ser Lys Ala Thr Ser Arg Ala
    690                 695                 700
Gln Phe Val Gln Arg Tyr Ala Val Leu Asp Lys Glu Phe Ser Glu Lys
705                 710                 715                 720
Asp Gly Asp Leu Thr Pro Thr Leu Lys Leu Lys Arg Ser Val Val Ala
                725                 730                 735
Lys Lys Gln Ala Ala Leu Ile Glu Ser Leu Tyr Lys
            740                 745

<210> SEQ ID NO 7
<211> LENGTH: 795
<212> TYPE: DNA
<213> ORGANISM: Artificial Sequence
<220> FEATURE:
<223> OTHER INFORMATION: Neomycin resistance gene

<400> SEQUENCE: 7
atgattgaac aagatggatt gcacgcaggt tctccggccg cttgggtgga gaggctattc    60
ggctatgact gggcacaaca gacaatcggc tgctctgatg ccgccgtgtt ccggctgtca   120

```
gcgcagggc gcccggttct ttttgtcaag accgacctgt ccggtgccct gaatgaactg    180
caggacgagg cagcgcggct atcgtggctg gccacgacgg gcgttccttg cgcagctgtg    240
ctcgacgttg gcactgaagc gggaagggac tggctgctat gggcgaagt gccggggcag     300 gatctcctgt catctcacct tgctcctgcc gagaaagtat ccatcatggc tgatgcaatg    360
cggcggctgc atacgcttga tccggctacc tgcccattcg accaccaagc gaaacatcgc    420
atcgagcgag cacgtactcg gatggaagcc ggtcttgtcg atcaggatga tctggacgaa    480
gagcatcagg ggctcgcgcc agccgaactg ttcgccaggc tcaaggcgcg catgcccgac    540
ggcgaggatc tcgtcgtgac ccatggcgat gcctgcttgc cgaatatcat ggtggaaaat    600
ggccgctttt ctggattcat cgactgtggc cggctgggtg tggcggaccg ctatcaggac    660
atagcgttgg ctacccgtga tattgctgaa gagcttggcg gcgaatgggc tgaccgcttc    720
ctcgtgcttt acggtatcgc cgctcccgat tcgcagcgca tcgccttcta tcgccttctt    780
gacgagttct tctga                                                    795

<210> SEQ ID NO 8
<211> LENGTH: 490
<212> TYPE: DNA
<213> ORGANISM: Artificial Sequence
<220> FEATURE:
<223> OTHER INFORMATION: Tubulin promoter

<400> SEQUENCE: 8
actgcgcatg gattgaccga cggccggttg ccaacttttg gggtcggccc cccttttcta     60
gcccttgccc gtccagcaat taaaaattat caacggcata ccggcactgg aagcttcggg    120
tttacaattt tggcttgcct tcctaatact gtaccgcgga gaacgtatga tattacagaa    180
aaatgccttg cacagttagc gcaaagggaa aacgtttctc cgccattgta cttttggaa     240 gagggaaagc gattgtaaaa tatggctctc cgctacgaga gtttgggctg ttgatacatg    300
tgaaaataag tgtggacgac tttgaatgac ttgatcaggc tgtttgcaca tataaccagc    360
gcgcatgcac ttctgacatg tcaatgacga aatttcacac ttcaccaata aattgtatcc    420
ttacgttttg tctttctcac acgcacatat atgatcatag ataaaagcca atatcaagaa    480
gctgtctttt                                                          490

<210> SEQ ID NO 9
<211> LENGTH: 35
<212> TYPE: DNA
<213> ORGANISM: Artificial Sequence
<220> FEATURE:
<223> OTHER INFORMATION: primer tub-neoF

<400> SEQUENCE: 9 tctttttgt gaagcatgat tgaacaagat ggatt                                35

<210> SEQ ID NO 10
<211> LENGTH: 35
<212> TYPE: DNA
<213> ORGANISM: Artificial Sequence
<220> FEATURE:
<223> OTHER INFORMATION: primer neo-hspR

<400> SEQUENCE: 10
tttcccccat cccgatcaga agaactcgtc aagaa                               35

<210> SEQ ID NO 11
```

```
<211> LENGTH: 35
<212> TYPE: DNA
<213> ORGANISM: Artificial Sequence
<220> FEATURE:
<223> OTHER INFORMATION: primer pUC-TUBpF

<400> SEQUENCE: 11
cgagctcggt acccgactgc gcatggattg accga                               35

<210> SEQ ID NO 12
<211> LENGTH: 20
<212> TYPE: DNA
<213> ORGANISM: Artificial Sequence
<220> FEATURE:
<223> OTHER INFORMATION: primer TuBpR

<400> SEQUENCE: 12
atatcaagaa gctgtctttt                                                20

<210> SEQ ID NO 13
<211> LENGTH: 25
<212> TYPE: DNA
<213> ORGANISM: Artificial Sequence
<220> FEATURE:
<223> OTHER INFORMATION: primer Thsp-F

<400> SEQUENCE: 13
tcgggatggg ggaaaaaaac ctctg                                          25

<210> SEQ ID NO 14
<211> LENGTH: 36
<212> TYPE: DNA
<213> ORGANISM: Artificial Sequence
<220> FEATURE:
<223> OTHER INFORMATION: primer pUC-Thsp-R

<400> SEQUENCE: 14
actctagagg atccccttc gtaaataaat cagctc                              36

<210> SEQ ID NO 15
<211> LENGTH: 1000
<212> TYPE: DNA
<213> ORGANISM: Nannochloropsis oculata

<400> SEQUENCE: 15
tcgggatggg ggaaaaaaac ctctgtgtgg gctgtcagtt gatactatta gaggtctttt    60
gttttgtttg tggctgcgtg tgtgtgtttg catgagaaat agacttgaga atatcggaag   120
gaactttgac atggtaaacg aggaaaagaa aatcttcaaa aaggaataat gggtaaaaac   180
aaggagcacc gggtctcttt agaaatgctt ctcggcggaa accagaaaaa aaggtagaa    240 tatgtcgact ttttcgctta tcattataga atgaaagatc gaatggccaa gggatttata   300
aattctttct ttatgttgtc gtagaactta ctttccatcc cgagggaggt gtatgcaggc   360
caaaccctct gacatgggcg caatatctct atgaaaggtt gttggaatac attgtccgac   420
ctccttcgag gcggagccgc atagttgaag tataggtgct tgcttcatcc atctcatgac   480
gctttgccag tgactcactc atgcatgtga cacatttagt tctgctcgct caagcctggc   540
ccctcctgac atgcacacat tgcacttgta ggtgggccac gtttagtata gacgccaccc   600
ctgtcgcacc atcggtccca gagcaggagc acgcttccct actcctgtac gctcccctg    660 cttccccccc tgctcgtcaa cgatggcgac gccagcggcc gcgaattaca gtgacggcgc   720
ggccgctcag gatgacagct cctctccttc aacatctccc aatcttccac cccgcccat    780
```

```
gtcgtcgttc gtacggccta tgctgaccga tatgtaccaa attacaatgg tcttcgcgta    840
ctggaagcaa aagcggcacc aggacagggc catctttgag ctcttttcc ggaagacacc    900 ctttaaggga gagtttgcca ttatggccgg cattgacgaa gtactcaagt acttggccca    960
ctttcgcttc tccgaggagg agctgattta tttacgaaag                        1000
```

<210> SEQ ID NO 16
<211> LENGTH: 35
<212> TYPE: DNA
<213> ORGANISM: Artificial Sequence
<220> FEATURE:
<223> OTHER INFORMATION: primer pUC19F

<400> SEQUENCE: 16

```
gggatcctct agagtcgacc tgcaggcatg caagc                               35
```

<210> SEQ ID NO 17
<211> LENGTH: 20
<212> TYPE: DNA
<213> ORGANISM: Artificial Sequence
<220> FEATURE:
<223> OTHER INFORMATION: primer pUC19R

<400> SEQUENCE: 17

```
cgggtaccga gctcgaattc                                                20
```

<210> SEQ ID NO 18
<211> LENGTH: 31
<212> TYPE: DNA
<213> ORGANISM: Artificial Sequence
<220> FEATURE:
<223> OTHER INFORMATION: primer VCPp-LACS2F

<400> SEQUENCE: 18

```
tccgagcaga ttatgcccgc ctacacgacg a                                   31
```

<210> SEQ ID NO 19
<211> LENGTH: 35
<212> TYPE: DNA
<213> ORGANISM: Artificial Sequence
<220> FEATURE:
<223> OTHER INFORMATION: primer LACS2-VCPtR

<400> SEQUENCE: 19

```
ctcttccaca gaagcctact tgtagagatt ggcga                               35
```

<210> SEQ ID NO 20
<211> LENGTH: 802
<212> TYPE: DNA
<213> ORGANISM: Nannochloropsis sp. W2J3B

<400> SEQUENCE: 20

```
ggcggtcttt tgtcctttcc tctatagccc gcccgtctag agggcacacg cgatgatctt    60
tatatctctt catgtgtctt tgttttaact aggatactgc cgggtgaatg cccatcggac    120
aagaggccaa actctatcta caccctttg acttctgttg tggtcgtagt gtgtgcttgc    180
atgccctgaa agtccaggca tcccacttgt gctctaaccc cattcaaaac agcagaagtg    240
cttaattaag atatagattc atgatctcct gtccctcct tcttaccttt tcacaaacct    300
cacacagaag tctccactct tcgcctctaa aacctctttt taaattatgg taagttcgtg    360
cggcagtggg ttttcggatc tatatttgtc aagatccagt tcaaggtcag ggatgtagat    420
```

```
taagtacaga aggagaagca caagcgcgcc agttcgcccc tcacggcctg gagcagggca    480
tttaatccct ctatcttacc agaaccatac tatacaacca atcctgttgg catcgctctg    540
tctatttgtc gtgcgtgcat gtgtccatgg tgtggtgggg ggcaggggtt ttcggggttg    600
cggttgaagg caccttatca gaaagatgcc ctcagagata gaggtagccc cctccccccg    660
atcttcgacc agtcctgtca ggcgaacact ttcacccgtc gttcacctcg ttacacacaa    720
ggagtagacc tctgaagttc taattgtcat aaatgcccct ccccccctccc tctttcccctt   780 gatcctcccc tccgagcaga tt                                            802

<210> SEQ ID NO 21
<211> LENGTH: 643
<212> TYPE: DNA
<213> ORGANISM: Nannochloropsis sp. W2J3B

<400> SEQUENCE: 21
gcttctgtgg aagagccagt ggtagtagca gtagcagcag cagtagcagc cgcagcactc     60
agtgttggcg cgagagattg tccatccctt cttaacctac cggaagagaa ataaggcctt    120
tctcccgtag ctgtcttcgt tgttttgtgc tgattgcttg atatgagagt gttgaattcc    180
tgcatcatgt ttttctctgt agtccttttcc tacccccgtc attttctttt ctccctggtt   240
cttcttttgt caccttatt ttacataaaa ttttctttgt ttatagtgag aggaaggtag    300 agagggaaa acaagaacaa cgaacgcaag cgtgtgaaag gagggcgagt agaagagaaa    360
cagatctgtt gagcattgag agtggagccg ggggaaaggc ttgtgtgttg tctttgaaaa    420
agttgtttaa atcacgaatc cgttagttct catgtgtacc tctttcacta catgtgatgg    480
agaaaacaaa agtgtgagga ttaattgaag aaaagaaga gttcgacacg tcaaaccgcc    540
caaaagacgt cacaaagaga acttgattct cttttgccgtg ttgatcctgt cttttccccc    600
agcttttctt gccacccgtg gcacacgaga tggacaagat cag                     643

<210> SEQ ID NO 22
<211> LENGTH: 37
<212> TYPE: DNA
<213> ORGANISM: Artificial Sequence
<220> FEATURE:
<223> OTHER INFORMATION: primer pUC-VCP1F

<400> SEQUENCE: 22
cgagctcggt acccgggcgg tcttttgtcc tttcctc                             37

<210> SEQ ID NO 23
<211> LENGTH: 22
<212> TYPE: DNA
<213> ORGANISM: Artificial Sequence
<220> FEATURE:
<223> OTHER INFORMATION: primer VCP1R

<400> SEQUENCE: 23
aatctgctcg gaggggagga tc                                             22

<210> SEQ ID NO 24
<211> LENGTH: 21
<212> TYPE: DNA
<213> ORGANISM: Artificial Sequence
<220> FEATURE:
<223> OTHER INFORMATION: primer VCP1tF

<400> SEQUENCE: 24
gcttctgtgg aagagccagt g                                              21
```

<210> SEQ ID NO 25
<211> LENGTH: 35
<212> TYPE: DNA
<213> ORGANISM: Artificial Sequence
<220> FEATURE:
<223> OTHER INFORMATION: primer VCP1t-TubR

<400> SEQUENCE: 25
caatccatgc gcagtctgat cttgtccatc tcgtg         35

<210> SEQ ID NO 26
<211> LENGTH: 20
<212> TYPE: DNA
<213> ORGANISM: Artificial Sequence
<220> FEATURE:
<223> OTHER INFORMATION: primer TubF

<400> SEQUENCE: 26
actgcgcatg gattgaccga         20

<210> SEQ ID NO 27
<211> LENGTH: 375
<212> TYPE: DNA
<213> ORGANISM: Artificial Sequence
<220> FEATURE:
<223> OTHER INFORMATION: Zeocin resistance gene

<400> SEQUENCE: 27
atggccaagc tgaccagcgc cgttccggtg ctcaccgcgc gcgacgtcgc cggagcggtc         60
gagttctgga ccgaccggct cgggttctcc cgggacttcg tggaggacga cttcgccggt        120
gtggtccggg acgacgtgac cctgttcatc agcgcggtcc aggaccaggt ggtgccggac        180
aacaccctgg cctgggtgtg ggtgcgcggc ctggacgagc tgtacgccga gtggtcggag        240
gtcgtgtcca cgaacttccg ggacgcctcc gggccggcca tgaccgagat cggcgagcag        300
ccgtgggggc gggagttcgc cctgcgcgac ccggccggca actgcgtgca cttcgtggcc        360
gaggagcagg actaa         375

<210> SEQ ID NO 28
<211> LENGTH: 32
<212> TYPE: DNA
<213> ORGANISM: Artificial Sequence
<220> FEATURE:
<223> OTHER INFORMATION: primer ble-TubF

<400> SEQUENCE: 28
tccgagcaga ttatggccaa gctgaccagc gc         32

<210> SEQ ID NO 29
<211> LENGTH: 36
<212> TYPE: DNA
<213> ORGANISM: Artificial Sequence
<220> FEATURE:
<223> OTHER INFORMATION: primer ble-HSPtR

<400> SEQUENCE: 29
tttcccccat cccgattagt cctgctcctc ggccac         36

<210> SEQ ID NO 30
<211> LENGTH: 38
<212> TYPE: DNA
<213> ORGANISM: Artificial Sequence
<220> FEATURE:

<223> OTHER INFORMATION: primer NTEF

<400> SEQUENCE: 30
gcggccgctc tagagtgcga acggcccac gccgggac         38

<210> SEQ ID NO 31
<211> LENGTH: 39
<212> TYPE: DNA
<213> ORGANISM: Artificial Sequence
<220> FEATURE:
<223> OTHER INFORMATION: primer NTER

<400> SEQUENCE: 31
acaaaatatt aacgcctagc taatatcaat tttctttgg         39

<210> SEQ ID NO 32
<211> LENGTH: 864
<212> TYPE: DNA
<213> ORGANISM: Nannochloropsis oculata

<400> SEQUENCE: 32

```
atgacgcctt tggccttcac ggtgctcggc aagcttggtg gcacgttgac ttttgcttgt      60
gtacgacgga ggctttatca cttgttacgg cgggcaactt tgtcctccca ttatcaggtc     120
actcggcctt acggtcacag caattccggc tgttcacata gcactaccac acttagaacc     180
agcttcccag tcctctttgc gcaattggca gcagccactg ctgccgtcgt cgctgccatt     240
tccctgccgt cgcctagtct atgcgagacg gcccacgccg ggactgagga gagacgaggt     300
gagaggaagg caatgaggga ggatggtgga aaaggcgagg ccacctcgtc tgctacatgc     360
aatccatcct tattcgaaca tcatgatcgc gtcgacacca agctgcatcg ggcctatcct     420
gaattcctga agttccacct tatccacgag acgctccgag gcaaagagaa aattgatggc     480
tacgaagttt acaaagacag gcgggatgat tcaattgtgg cgtatgctcg ccttggcaaa     540
ctgctgagcg acaccccga cataatccac ggagggtcca ttgcggcttt gctgacaat      600
accatgggag ttgcctttt cgccgccaag cgtggcaatg gttttacagc aaatctcacc      660
atcaactaca gcgacccat acgtgtggc accgaagtca agttttagc tcgagtagag      720
aaggtggaag ggcgcaaggt cttcttgcgg gccgagattc gagacgctaa ggatgaggct     780
atcctctaca ctgaagccaa atccctcttc atcacgtctc aaagtccttt attgaagggc     840
ccaaagaaaa ttgatattag ctag                                            864
```

<210> SEQ ID NO 33
<211> LENGTH: 287
<212> TYPE: PRT
<213> ORGANISM: Nannochloropsis oculata

<400> SEQUENCE: 33

Met Thr Pro Leu Ala Phe Thr Val Leu Gly Lys Leu Gly Gly Thr Leu
1               5                   10                  15

Thr Phe Ala Cys Val Arg Arg Arg Leu Tyr His Leu Leu Arg Arg Ala
            20                  25                  30

Thr Leu Ser Ser His Tyr Gln Val Thr Arg Pro Tyr Gly His Ser Asn
        35                  40                  45

Ser Gly Cys Ser His Ser Thr Thr Thr Leu Arg Thr Ser Phe Pro Val
    50                  55                  60

Leu Phe Ala Gln Leu Ala Ala Ala Thr Ala Ala Val Val Ala Ala Ile
65                  70                  75                  80

```
Ser Leu Pro Ser Pro Ser Leu Cys Glu Thr Ala His Ala Gly Thr Glu
                85                  90                  95

Glu Arg Arg Gly Glu Arg Lys Ala Met Arg Glu Asp Gly Gly Lys Gly
            100                 105                 110

Glu Ala Thr Ser Ser Ala Thr Cys Asn Pro Ser Leu Phe Glu His His
        115                 120                 125

Asp Arg Val Asp Thr Lys Leu His Arg Ala Tyr Pro Glu Phe Leu Lys
    130                 135                 140

Phe His Leu Ile His Glu Thr Leu Arg Gly Lys Glu Lys Ile Asp Gly
145                 150                 155                 160

Tyr Glu Val Tyr Lys Asp Arg Arg Asp Asp Ser Ile Val Ala Tyr Ala
                165                 170                 175

Arg Leu Gly Lys Leu Leu Ser Gly His Pro Asp Ile Ile His Gly Gly
            180                 185                 190

Ser Ile Ala Ala Leu Leu Asp Asn Thr Met Gly Val Ala Phe Phe Ala
        195                 200                 205

Ala Lys Arg Gly Asn Gly Phe Thr Ala Asn Leu Thr Ile Asn Tyr Lys
    210                 215                 220

Arg Pro Ile Thr Cys Gly Thr Glu Val Lys Val Leu Ala Arg Val Glu
225                 230                 235                 240

Lys Val Glu Gly Arg Lys Val Phe Leu Arg Ala Glu Ile Arg Asp Ala
                245                 250                 255

Lys Asp Glu Ala Ile Leu Tyr Thr Glu Ala Lys Ser Leu Phe Ile Thr
            260                 265                 270

Ser Gln Ser Pro Leu Leu Lys Gly Pro Lys Lys Ile Asp Ile Ser
        275                 280                 285

<210> SEQ ID NO 34
<211> LENGTH: 19
<212> TYPE: DNA
<213> ORGANISM: Artificial Sequence
<220> FEATURE:
<223> OTHER INFORMATION: primer pBSR

<400> SEQUENCE: 34
tctagagcgg ccgccaccg                                              19

<210> SEQ ID NO 35
<211> LENGTH: 24
<212> TYPE: DNA
<213> ORGANISM: Artificial Sequence
<220> FEATURE:
<223> OTHER INFORMATION: primer pBSF

<400> SEQUENCE: 35
gcgttaatat tttgttaaaa ttcg                                        24

<210> SEQ ID NO 36
<211> LENGTH: 39
<212> TYPE: DNA
<213> ORGANISM: Artificial Sequence
<220> FEATURE:
<223> OTHER INFORMATION: primer NTE(VW)F

<400> SEQUENCE: 36
ctggacaata ccatgggatg ggcctttttc gccgccaag                        39

<210> SEQ ID NO 37
<211> LENGTH: 20
<212> TYPE: DNA
```

```
<213> ORGANISM: Artificial Sequence
<220> FEATURE:
<223> OTHER INFORMATION: primer NTE(VW)R

<400> SEQUENCE: 37
catggtattg tccagcaaag                                              20

<210> SEQ ID NO 38
<211> LENGTH: 603
<212> TYPE: DNA
<213> ORGANISM: Nannochloropsis oculata

<400> SEQUENCE: 38
tgcgagacgg cccacgccgg gactgaggag agacgaggtg agaggaaggc aatgagggag    60
gatggtggaa aaggcgaggc cacctcgtct gctacatgca atccatcctt attcgaacat   120
catgatcgcg tcgacaccaa gctgcatcgg gcctatcctg aattcctgaa gttccacctt   180
atccacgaga cgctccgagg caaagagaaa attgatggct acgaagttta caaagacagg   240
cgggatgatt caattgtggc gtatgctcgc cttggcaaac tgctgagcgg acaccccgac   300
ataatccacg gagggtccat tgcggctttg ctggacaata ccatgggatg gccttttttc   360
gccgccaagc gtggcaatgg ttttacagca aatctcacca tcaactacaa gcgacccatc   420
acgtgtggca ccgaagtcaa agttttagct cgagtagaga aggtggaagg cgcaaggtc    480 ttcttgcggg ccgagattcg agacgctaag gatgaggcta tcctctacac tgaagccaaa   540
tccctcttca tcacgtctca aagtccttta ttgaagggcc caagaaaaat tgatattagc   600
tag                                                                603

<210> SEQ ID NO 39
<211> LENGTH: 35
<212> TYPE: DNA
<213> ORGANISM: Artificial Sequence
<220> FEATURE:
<223> OTHER INFORMATION: primer VCP(TP)-NTEF

<400> SEQUENCE: 39
ccgcggtgtt gcgcgctgcg agacggccca cgccg                             35

<210> SEQ ID NO 40
<211> LENGTH: 35
<212> TYPE: DNA
<213> ORGANISM: Artificial Sequence
<220> FEATURE:
<223> OTHER INFORMATION: primer VCPt-NTER

<400> SEQUENCE: 40
ctcttccaca gaagcctagc taatatcaat tttct                             35

<210> SEQ ID NO 41
<211> LENGTH: 99
<212> TYPE: DNA
<213> ORGANISM: Nannochloropsis sp. W2J3B

<400> SEQUENCE: 41
atgaagaccg ccgctctcct cactgtctcc accctcatgg gcgcccaggc ctttatggcc    60
cccgccccca agttctcccg cacccgcggt gttgcgcgc                          99

<210> SEQ ID NO 42
<211> LENGTH: 36
<212> TYPE: DNA
<213> ORGANISM: Artificial Sequence
```

<220> FEATURE:
<223> OTHER INFORMATION: primer VCPp-VCP(TP)F

<400> SEQUENCE: 42 cctccgagc agattatgaa gaccgccgct ctcctc					36

<210> SEQ ID NO 43
<211> LENGTH: 28
<212> TYPE: DNA
<213> ORGANISM: Artificial Sequence
<220> FEATURE:
<223> OTHER INFORMATION: primer VCP(TP)R

<400> SEQUENCE: 43
gttctcccgc acccgcggtg ttgcgcgc					28

<210> SEQ ID NO 44
<211> LENGTH: 32
<212> TYPE: DNA
<213> ORGANISM: Artificial Sequence
<220> FEATURE:
<223> OTHER INFORMATION: primer VCP-LACS6F

<400> SEQUENCE: 44
tccgagcaga ttatggcgct cttggccagg tg					32

<210> SEQ ID NO 45
<211> LENGTH: 35
<212> TYPE: DNA
<213> ORGANISM: Artificial Sequence
<220> FEATURE:
<223> OTHER INFORMATION: primer LACS6-VCPR

<400> SEQUENCE: 45
ctcttccaca gaagcttaca tctcctctat ttcca					35

<210> SEQ ID NO 46
<211> LENGTH: 1149
<212> TYPE: DNA
<213> ORGANISM: Umbellularia californica

<400> SEQUENCE: 46

| | | |
|---|---|---|
| atggccacca cctctttagc ttccgctttc tgctcgatga aagctgtaat gttggctcgt | 60 |
| gatggccggg gcatgaaacc caggagcagt gatttgcagc tgagggcggg aaatgcgcca | 120 |
| acctctttga agatgatcaa tgggaccaag ttcagttaca cggagagctt gaaaaggttg | 180 |
| cctgactgga gcatgctctt tgcagtgatc acaaccatct tttcggctgc tgagaagcag | 240 |
| tggaccaatc tagagtggaa gccgaagccg aagctacccc agttgcttga tgaccatttt | 300 |
| ggactgcatg gttagttttc aggcgcacc tttgccatca gatcttatga ggtgggacct | 360 |
| gaccgctcca catctatact ggctgttatg aatcacatgc aggaggctac acttaatcat | 420 |
| gcgaagagtg tgggaattct aggagatgga ttcgggacga cgctagagat gagtaagaga | 480 |
| gatctgatgt gggttgtgag acgcacgcat gttgctgtgg aacggtaccc tacttggggt | 540 |
| gatactgtag aagtagagtg ctggattggt gcatctggaa ataatggcat gcgacgtgat | 600 |
| ttccttgtcc gggactgcaa acaggcgaa attcttacaa gatgtaccag cctttcggtg | 660 |
| ctgatgaata caaggacaag gaggttgtcc acaatccctg acgaagttag aggggagata | 720 |
| gggcctgcat tcattgataa tgtggctgtc aaggacgatg aaattaagaa actacagaag | 780 |
| ctcaatgaca gcactgcaga ttacatccaa ggaggtttga ctcctcgatg gaatgatttg | 840 |

```
gatgtcaatc agcatgtgaa caacctcaaa tacgttgcct gggttttga gaccgtccca    900 gactccatct tgagagtca tcatatttcc agcttcactc ttgaatacag gagagagtgc    960
acgagggata gcgtgctgcg gtccctgacc actgtctctg gtggctcgtc ggaggctggg   1020
ttagtgtgcg atcacttgct ccagcttgaa ggtgggtctg aggtattgag ggcaagaaca   1080
gagtggaggc ctaagcttac cgatagtttc agagggatta gtgtgatacc cgcagaaccg   1140
agggtgtaa                                                          1149
```

<210> SEQ ID NO 47
<211> LENGTH: 382
<212> TYPE: PRT
<213> ORGANISM: Umbellularia californica

<400> SEQUENCE: 47

```
Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
            20                  25                  30

Gln Leu Arg Ala Gly Asn Ala Pro Thr Ser Leu Lys Met Ile Asn Gly
        35                  40                  45

Thr Lys Phe Ser Tyr Thr Glu Ser Leu Lys Arg Leu Pro Asp Trp Ser
    50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Lys Leu Pro Gln Leu Leu
                85                  90                  95

Asp Asp His Phe Gly Leu His Gly Leu Val Phe Arg Arg Thr Phe Ala
            100                 105                 110

Ile Arg Ser Tyr Glu Val Gly Pro Asp Arg Ser Thr Ser Ile Leu Ala
        115                 120                 125

Val Met Asn His Met Gln Glu Ala Thr Leu Asn His Ala Lys Ser Val
    130                 135                 140

Gly Ile Leu Gly Asp Gly Phe Gly Thr Thr Leu Glu Met Ser Lys Arg
145                 150                 155                 160

Asp Leu Met Trp Val Val Arg Arg Thr His Val Ala Val Glu Arg Tyr
                165                 170                 175

Pro Thr Trp Gly Asp Thr Val Glu Val Glu Cys Trp Ile Gly Ala Ser
            180                 185                 190

Gly Asn Asn Gly Met Arg Arg Asp Phe Leu Val Arg Asp Cys Lys Thr
        195                 200                 205

Gly Glu Ile Leu Thr Arg Cys Thr Ser Leu Ser Val Leu Met Asn Thr
    210                 215                 220

Arg Thr Arg Arg Leu Ser Thr Ile Pro Asp Glu Val Arg Gly Glu Ile
225                 230                 235                 240

Gly Pro Ala Phe Ile Asp Asn Val Ala Val Lys Asp Asp Glu Ile Lys
                245                 250                 255

Lys Leu Gln Lys Leu Asn Asp Ser Thr Ala Asp Tyr Ile Gln Gly Gly
            260                 265                 270

Leu Thr Pro Arg Trp Asn Asp Leu Asp Val Asn Gln His Val Asn Asn
        275                 280                 285

Leu Lys Tyr Val Ala Trp Val Phe Glu Thr Val Pro Asp Ser Ile Phe
    290                 295                 300

Glu Ser His His Ile Ser Ser Phe Thr Leu Glu Tyr Arg Arg Glu Cys
305                 310                 315                 320
```

Thr Arg Asp Ser Val Leu Arg Ser Leu Thr Thr Val Ser Gly Gly Ser
            325                 330                 335

Ser Glu Ala Gly Leu Val Cys Asp His Leu Leu Gln Leu Glu Gly Gly
            340                 345                 350

Ser Glu Val Leu Arg Ala Arg Thr Glu Trp Arg Pro Lys Leu Thr Asp
            355                 360                 365

Ser Phe Arg Gly Ile Ser Val Ile Pro Ala Glu Pro Arg Val
            370                 375                 380

<210> SEQ ID NO 48
<211> LENGTH: 35
<212> TYPE: DNA
<213> ORGANISM: Artificial Sequence
<220> FEATURE:
<223> OTHER INFORMATION: primer BTE-VCP(TP)F

<400> SEQUENCE: 48
cgcggtgttg cgcgctggaa gccgaagccg aagct                          35

<210> SEQ ID NO 49
<211> LENGTH: 35
<212> TYPE: DNA
<213> ORGANISM: Artificial Sequence
<220> FEATURE:
<223> OTHER INFORMATION: primer BTE-VCPtR

<400> SEQUENCE: 49
ctcttccaca gaagcttaca ccctcggttc tgcgg                          35

<210> SEQ ID NO 50
<211> LENGTH: 32
<212> TYPE: DNA
<213> ORGANISM: Artificial Sequence
<220> FEATURE:
<223> OTHER INFORMATION: primer VCP-LACS11F

<400> SEQUENCE: 50
tccgagcaga ttatgggcaa tacaccctcc ga                             32

<210> SEQ ID NO 51
<211> LENGTH: 37
<212> TYPE: DNA
<213> ORGANISM: Artificial Sequence
<220> FEATURE:
<223> OTHER INFORMATION: primer LACS11-VCPR

<400> SEQUENCE: 51
ctcttccaca gaagctcatt tgtacagaga ctcgatg                        37

<210> SEQ ID NO 52
<211> LENGTH: 1000
<212> TYPE: DNA
<213> ORGANISM: Nannochloropsis oculata

<400> SEQUENCE: 52
gcaagggaca gcagggatgg gaatggcaat gccgattgtc gtacggccaa aaactggagc      60
tctggaagag cgtcactcaa cggtcgattc ccaacgcaca ctggacaact tttctgcata    120
aaaaaactca agaaaaggcc agttcaactg aataaatcaa ctagttgtca ataatccata    180
cttttggtta aattttcgtc gcgcatgacg aggacccggc gaccaatgcc tggtttgaag    240
gtgtgcttta tctcggggac cgacaactat cgagttgaat gagcatcgtg tggacccgga    300

| | |
|---|---|
| cgaacgccac acccagacaa gcaccaatct ccgaacctttt tggcgtagct gttggcctag | 360 |
| acattgtcat tgcaaatcta gagtgccgac tggaggcata tgcctcagtt ttattcacaa | 420 |
| caatgcacga tcccagctcc atggcccatt gagtggccgc ctctgcccgt cttcctctcc | 480 |
| tctcgcgatc gccatctccc atctccgtcg ccgcaacaaa gatggaagaa ttccacgatt | 540 |
| tctggtgcat gcttgccttc acactcactt ttcggtgtcc attgtactgt cttaaggtcg | 600 |
| tgacgtttac acaaggcctg tgtatgctgc tctggcagca gatccgcttc ttgttcttcg | 660 |
| attcgccagg ttaaagccac gcacaaatgc agcacgctcc cgttagagct taatgcacag | 720 |
| aacaaggaag aaggaatgat gactttctcc tttcatttga catgtctgcc cacggagttt | 780 |
| tgtttcttgg tctccgacat ctattcgtcc tcaaagtggc ttggtcgccc gccagctgcg | 840 |
| tctatctgac ccctgtctca ccccgtgact cgcccggtta gccttactca cctcaacggt | 900 |
| taaactagca tactcacctc tcatgtcctt ctacacacac aactgcagga ccacctcata | 960 |
| acccgaagca agcaaacatc ttcaagtgag agaagaaagc | 1000 |

```
<210> SEQ ID NO 53
<211> LENGTH: 1000
<212> TYPE: DNA
<213> ORGANISM: Nannochloropsis oculata

<400> SEQUENCE: 53
```

| | |
|---|---|
| tccgcgcagt atcgcagcaa accatgcacg tccaccagat actccccatc aggtaagtga | 60 |
| aaaccatgct gcttccacat gtgcaacaca gttgactcca cgctcgggca tcgctcgttg | 120 |
| caaaagatgc aaacctcagg gctcaggtct accggtgcag cagcccccgcc ttcctcctcc | 180 |
| cctgccttat tgctggcctc gtccatggcc gcctcatcca tagagccggg taccttgatc | 240 |
| gtcgttgggg tggagggcgc tacagtagct tttaccttgg tgggggtacc accgttgtcg | 300 |
| ccctccgcca tggtgaggtg cttgcgggac ttgagatgct ggctcagcgt ggccttagag | 360 |
| gcaaaggagc ggttgcagag atggcattta gcgtgaaagg cctcggtagt cgatttgctc | 420 |
| atcccagcca agctctgggc ggcggctttg cggcgttgat attcagtttc actgacaggc | 480 |
| cccaggtcgt tggtgcggcg cttcagattg tatcggtgga gctccatgcg atagtgctct | 540 |
| ttgtgagcga cggatgaatc gaatcccagg ccacatgtct gacatttgag gaggtccatg | 600 |
| ttacccgagt gcgcgtgcgt tgggtgaaaa agacccccgtg cgttgcgcgg tgtgggaag | 660 |
| ccggcgggca aggtgctgcg gtgcgtacgc ggacgggatg tgttttgatt gagtggtgat | 720 |
| gcgtggatag attgacaaaa cgagagctgt ctcacttagc ccttccagtt ggtgccttgg | 780 |
| caaggacatc agactacatc caggggtctt tggtggtcag ggtgcaggtc agattttgat | 840 |
| tttcctggtg cgagttgggg ctaccctctt ggctctgcca caagtctcaa agttcctcgt | 900 |
| ttgagcacag gatgcctcac actcacgcat ttcaattatt ttatgccata ttttacgcac | 960 |
| agatgtgacc gcacttgcgg tgctatatcg ccaagctggg | 1000 |

```
<210> SEQ ID NO 54
<211> LENGTH: 1000
<212> TYPE: DNA
<213> ORGANISM: Nannochloropsis oculata

<400> SEQUENCE: 54
```

| | |
|---|---|
| aaagaggaag tacaagacga agagagtgga atagaagact aaagagaaga tttaaaaaga | 60 |
| agaactgcaa ttaactcaaa tattattaat tatcacgaag cctcttgccc cttacgcctc | 120 |
| attctctata cagttttccc cccggctctg ctcagctttc cccccctctt tttttcctcc | 180 |

```
ttgcctttgt ggtctgttta gttttccag gtcaggggaa gtatttgtga gaatgtaacg      240
tatgagcctg tcatacgcaa tgttaccatc caaatgcctc attggaggcg cacagcacat      300
gctgaaaccc catccttcac acttatgtac acagtggccg tcgcgggttt cgatctgccc      360
acttcagcag cactcctgaa gtccaatccc gcatgcgtca ctgcgttaaa ttctctgtca      420
acctcggcag gcatgtaaat tgcaagcttg tacgcccta atgaggacca cacggcgctt      480
tgggtgccgc ttgctttgca tgtgaatatc gtagattttt atgtttattt tttcaaaaag      540
agggacgacg acgcgattcg tctctggctg ggccgaggtg cctcgctcgc taaaacttg      600 tgatgacgat gacgatccac aggcggactc atttataatc cttcagcctc ttgcgtgcat      660
gcaacaacca tcgagtctgt atgccccgat gccctgctca gtaaacatat aagtccctct      720
tgtcatgtgt gaaagtgatg gctatgttgg gagaaggaca aggaatagac agacccgcca      780
aaccacatgc ccccccttct tttaaaaag atcatgaccc tcaccagaag gccaacacac       840
cgattcaagc ttacccggtc cctcacccct ttcaccttca tcttcgtata gtctgtcaaa      900
agacagccaa cgaagcaagg ccctaaccca ggaacagcat ccaagcaggc ttccccctg       960 acactctgcc tgcctacccg cactcctgcc taaaaccttt                            1000
```

```
<210> SEQ ID NO 55
<211> LENGTH: 960
<212> TYPE: DNA
<213> ORGANISM: Cocos nucifera

<400> SEQUENCE: 55
atgaccatga ttacgccaag cttgcatgcc tgcaggtcga ctctagagct cgattccaag       60 aagaggggg ccgacgcggt cgcagatgcc tctggggtcg ggaagatggt caagaatgga      120
cttgtttaca ggcagaattt ttctatccgg tcctacgaaa tcggggttga taaacgtgct      180
tcggtagagg cattgatgaa tcatttccag gaaacgtcgc ttaaccattg caagtgtatt      240
ggccttatgc atggcggctt tggttgtaca ccagagatga ctcgaagaaa tctgatatgg      300
gttgttgcca aaatgctggt tcatgtcgaa cgttatcctt ggtggggaga cgtggttcaa      360
ataaatacgt ggattagttc atctggaaag aatggtatgg gacgtgattg gcatgttcat      420
gactgccaaa ctggcctacc tattatgagg ggtaccagtg tctgggtcat gatggataaa      480
cacacgagga gactgtctaa acttcctgaa gaagttagag cagagataac ccctttcttt      540
tcagagcgtg atgctgtttt ggacgataac ggcagaaaac ttcccaagtt cgatgatgat      600
tctgcagctc atgttcgaag gggcttgact cctcgttggc atgatttcga tgtaaatcag      660
catgtgaaca atgtcaaata cgtcggctgg attcttgaga gcgttcctgt gtggatgttg      720
gatggctacg aggttgcaac catgagtctg aataccgga gggagtgtag gatggatagt       780
gtggtgcagt ctctcaccgc cgtctcttcc gaccacgccg acggctcccc catcgtgtgc      840
cagcatcttc tgcggctcga ggatgggact gagattgtga gggtcaaac agaatggagg      900 cctaagcagc aggcttgtga tcttgggaac atgggtctgc acccaactga gagtaaatga      960
```

```
<210> SEQ ID NO 56
<211> LENGTH: 319
<212> TYPE: PRT
<213> ORGANISM: Cocos nucifera

<400> SEQUENCE: 56

Met Thr Met Ile Thr Pro Ser Leu His Ala Cys Arg Ser Thr Leu Glu
1               5                   10                  15
```

Leu Asp Ser Lys Lys Arg Gly Ala Asp Ala Val Ala Asp Ala Ser Gly
            20                  25                  30

Val Gly Lys Met Val Lys Asn Gly Leu Val Tyr Arg Gln Asn Phe Ser
        35                  40                  45

Ile Arg Ser Tyr Glu Ile Gly Val Asp Lys Arg Ala Ser Val Glu Ala
50                  55                  60

Leu Met Asn His Phe Gln Glu Thr Ser Leu Asn His Cys Lys Cys Ile
65                  70                  75                  80

Gly Leu Met His Gly Gly Phe Gly Cys Thr Pro Glu Met Thr Arg Arg
                85                  90                  95

Asn Leu Ile Trp Val Val Ala Lys Met Leu Val His Val Glu Arg Tyr
            100                 105                 110

Pro Trp Trp Gly Asp Val Val Gln Ile Asn Thr Trp Ile Ser Ser Ser
        115                 120                 125

Gly Lys Asn Gly Met Gly Arg Asp Trp His Val His Asp Cys Gln Thr
130                 135                 140

Gly Leu Pro Ile Met Arg Gly Thr Ser Val Trp Val Met Met Asp Lys
145                 150                 155                 160

His Thr Arg Arg Leu Ser Lys Leu Pro Glu Glu Val Arg Ala Glu Ile
                165                 170                 175

Thr Pro Phe Phe Ser Glu Arg Asp Ala Val Leu Asp Asp Asn Gly Arg
            180                 185                 190

Lys Leu Pro Lys Phe Asp Asp Ser Ala Ala His Val Arg Arg Gly
        195                 200                 205

Leu Thr Pro Arg Trp His Asp Phe Asp Val Asn Gln His Val Asn Asn
210                 215                 220

Val Lys Tyr Val Gly Trp Ile Leu Glu Ser Val Pro Val Trp Met Leu
225                 230                 235                 240

Asp Gly Tyr Glu Val Ala Thr Met Ser Leu Glu Tyr Arg Arg Glu Cys
                245                 250                 255

Arg Met Asp Ser Val Val Gln Ser Leu Thr Ala Val Ser Ser Asp His
            260                 265                 270

Ala Asp Gly Ser Pro Ile Val Cys Gln His Leu Leu Arg Leu Glu Asp
        275                 280                 285

Gly Thr Glu Ile Val Arg Gly Gln Thr Glu Trp Arg Pro Lys Gln Gln
290                 295                 300

Ala Cys Asp Leu Gly Asn Met Gly Leu His Pro Thr Glu Ser Lys
305                 310                 315

<210> SEQ ID NO 57
<211> LENGTH: 825
<212> TYPE: DNA
<213> ORGANISM: Nannochloropsis gaditana

<400> SEQUENCE: 57
atgctatgtt gcgcctgtaa atcagtgcat gcgactatta gtgtcgcctt tattggtact      60
cggaagccac atcgtttgcc tgcattgttt ccattgttcc ttgccccggc ccgagcactc     120
agccatcagg agccgaaccc tgcaacgtgc gggacgcaaa actcatcctt ctcgatcttg     180
ttgaaaacgg tagtagcagg atcattcgtc ggtgcggcat tcatcgctgg catacagca      240 ggggctagct gtgatgaagt aaagtctccg caggaggtga acaatgtagg aggcggcgcc     300
ccagtgactg cccctacac ggtcactttt gcgtccaatt atcatgatcg agtggacaca      360
aaacttcata gagcttatcc tgagttttta cagtaccatc ttattcatga aacgcttcga     420

```
ggcaaggaaa agatagaggg ctacgaggtg tacaaagata ggcgtgacga ttctatcgta      480
gcatttgctc gcctcgggaa gcttctcagc gggcatccgg atataatcca tggaggctct      540
atagccgcct tactcgacaa cactatgggc gtggcattct tcgctgccaa taaaggtaat      600
ggcttcactg ccaacctcac aatcaattac aagaggccga tcatttgtgg caccgagatc      660
aaggtcttgg cccgagtgga gcggtttgaa ggacgcaagg ttttcctacg agcagagatt      720
cgagatgcta aggacgaggc agtgttgtac acggaagcca catccctctt cataacttca      780
caaagtcctc tgcttacggg accgaagaag gtggacatca gttag                     825
```

```
<210> SEQ ID NO 58
<211> LENGTH: 274
<212> TYPE: PRT
<213> ORGANISM: Nannochloropsis gaditana

<400> SEQUENCE: 58

Met Leu Cys Cys Ala Cys Lys Ser Val His Ala Thr Ile Ser Val Ala
  1               5                  10                  15

Phe Ile Gly Thr Arg Lys Pro His Arg Leu Pro Ala Leu Phe Pro Leu
                 20                  25                  30

Phe Leu Ala Pro Ala Arg Ala Leu Ser His Gln Glu Pro Asn Pro Ala
             35                  40                  45

Thr Cys Gly Thr Gln Asn Ser Ser Phe Ser Ile Leu Leu Lys Thr Val
         50                  55                  60

Val Ala Gly Ser Phe Val Gly Ala Ala Phe Ile Ala Gly His Thr Ala
 65                  70                  75                  80

Gly Ala Ser Cys Asp Glu Val Lys Ser Pro Gln Glu Val Asn Asn Val
                 85                  90                  95

Gly Gly Gly Ala Pro Val Thr Ala Pro Tyr Thr Val Thr Phe Ala Ser
            100                 105                 110

Asn Tyr His Asp Arg Val Asp Thr Lys Leu His Arg Ala Tyr Pro Glu
            115                 120                 125

Phe Leu Gln Tyr His Leu Ile His Glu Thr Leu Arg Gly Lys Glu Lys
        130                 135                 140

Ile Glu Gly Tyr Glu Val Tyr Lys Asp Arg Arg Asp Asp Ser Ile Val
145                 150                 155                 160

Ala Phe Ala Arg Leu Gly Lys Leu Leu Ser Gly His Pro Asp Ile Ile
                165                 170                 175

His Gly Gly Ser Ile Ala Ala Leu Leu Asp Asn Thr Met Gly Val Ala
            180                 185                 190

Phe Phe Ala Ala Asn Lys Gly Asn Gly Phe Thr Ala Asn Leu Thr Ile
        195                 200                 205

Asn Tyr Lys Arg Pro Ile Ile Cys Gly Thr Glu Ile Lys Val Leu Ala
    210                 215                 220

Arg Val Glu Arg Phe Glu Gly Arg Lys Val Phe Leu Arg Ala Glu Ile
225                 230                 235                 240

Arg Asp Ala Lys Asp Glu Ala Val Leu Tyr Thr Glu Ala Thr Ser Leu
                245                 250                 255

Phe Ile Thr Ser Gln Ser Pro Leu Leu Thr Gly Pro Lys Lys Val Asp
            260                 265                 270

Ile Ser

<210> SEQ ID NO 59
<211> LENGTH: 858
```

<212> TYPE: DNA
<213> ORGANISM: Nannochloropsis granulata

<400> SEQUENCE: 59

```
atgacgcctt tggccttcac ggcgctcggc gaggtcggtg gcatgttggc tgctgcctgt      60
gtacgacgga agcttcatca cttgttgcgg cgggcagctt cgtcctccca ggtcactcga     120
ccttacagtc acagcaccgc caacagcaca catagcacca ccacacttag caacagcttt     180
ccagtcctct tgcgcaact cgcagcagcc gctgctgccg tcatggctgc cacttccctg      240
tcgtcgccca gtctatgtga cacggcccac accaatactg aggagagagg aggcgaaggg     300
gaggcaatga gggagaaggg tggggaaggc gaggccactt cgtctgctac atgcgctcca     360
tctttcttcg agcatcatga tcgcgtcgac acgaagctgc atcgggccta tcccgagttt     420
ctgaagttcc acctcatcca cgagacgctc cgagggaaag agaaaattga tggctacgaa     480
gtatacaaaa acaggcggga cgattcagtt gtggcgtatg ctcgcctggg caaactgctg     540
agcggacacc ctgacataat tcacggaggg tccatcgctg ctttgctgga acaccatg      600
ggagttgcct ttttcgccgc caagcgcggc aatggtttca cagcaaatct caccatcaac     660
tacaagcgac ccatcacgtg tggcaccgag gtcaaagttc tggctcgagt agagaaggtg     720
gaggggcgca aggtcttttt cgggctgag atcagggacg ccaaggatga ggctatcctt      780
tacactgaag ccaactccct cttcatcacg tcgcaaagcc ctctattgaa gggcccaaag     840
aaaattgaca ttagctag                                                   858
```

<210> SEQ ID NO 60
<211> LENGTH: 285
<212> TYPE: PRT
<213> ORGANISM: Nannochloropsis granulata

<400> SEQUENCE: 60

```
Met Thr Pro Leu Ala Phe Thr Ala Leu Gly Glu Val Gly Gly Met Leu
1               5                   10                  15

Ala Ala Ala Cys Val Arg Arg Lys Leu His His Leu Leu Arg Arg Ala
            20                  25                  30

Ala Ser Ser Gln Val Thr Arg Pro Tyr Ser His Ser Thr Ala Asn
        35                  40                  45

Ser Thr His Ser Thr Thr Thr Leu Ser Asn Ser Phe Pro Val Leu Phe
    50                  55                  60

Ala Gln Leu Ala Ala Ala Ala Ala Val Met Ala Ala Thr Ser Leu
65                  70                  75                  80

Ser Ser Pro Ser Leu Cys Glu Thr Ala His Thr Asn Thr Glu Glu Arg
                85                  90                  95

Gly Gly Glu Gly Glu Ala Met Arg Glu Lys Gly Gly Glu Gly Glu Ala
            100                 105                 110

Thr Ser Ser Ala Thr Cys Ala Pro Ser Phe Phe Glu His His Asp Arg
        115                 120                 125

Val Asp Thr Lys Leu His Arg Ala Tyr Pro Glu Phe Leu Lys Phe His
    130                 135                 140

Leu Ile His Glu Thr Leu Arg Gly Lys Glu Lys Ile Asp Gly Tyr Glu
145                 150                 155                 160

Val Tyr Lys Asn Arg Arg Asp Asp Ser Val Val Ala Tyr Ala Arg Leu
                165                 170                 175

Gly Lys Leu Leu Ser Gly His Pro Asp Ile Ile His Gly Gly Ser Ile
            180                 185                 190
```

```
Ala Ala Leu Leu Asp Asn Thr Met Gly Val Ala Phe Phe Ala Ala Lys
        195                 200                 205

Arg Gly Asn Gly Phe Thr Ala Asn Leu Thr Ile Asn Tyr Lys Arg Pro
    210                 215                 220

Ile Thr Cys Gly Thr Glu Val Lys Val Leu Ala Arg Val Glu Lys Val
225                 230                 235                 240

Glu Gly Arg Lys Val Phe Leu Arg Ala Glu Ile Arg Asp Ala Lys Asp
                245                 250                 255

Glu Ala Ile Leu Tyr Thr Glu Ala Asn Ser Leu Phe Ile Thr Ser Gln
            260                 265                 270

Ser Pro Leu Leu Lys Gly Pro Lys Lys Ile Asp Ile Ser
        275                 280                 285

<210> SEQ ID NO 61
<211> LENGTH: 702
<212> TYPE: DNA
<213> ORGANISM: Symbiodinium microadriaticum

<400> SEQUENCE: 61
atggctttca ggctatgctc tctttcccgg cggtttgctg cgcacgcgca gcaggtgctg      60
cggaaggagg ctggctttga gttccgcgca agctgcatcg ccattaccgc tggcatctct     120
gctggatggt gcatgcagca ggcagcgcgg cggagggca tctggactcc gcacctgggc      180
gaggaggcca agttgttgaa cctccagcgc gagatggcgc tgagagacag acacgacaag     240
caatttgtgt ggcagaccctg cagtggccag ggcaaaattg aggactgccg catatatcac    300
tgcaagcgag aagaagttga tcgtgaggtt cgctggacg cgccggaaat ggtggagggc      360
aaaacacgga tttgtgcagt gatgcgcgtt ggcgacgagc tgaacggcca tcctgggctt     420
ttgcatggcg gcttcactgc cgccgtgctg acgatttca caggcctggc gacctggatg      480
gagaagcaag cgcaggcgct ggacaaggat gcggccattt tcaccgctca catggatctc     540
agctatcggc gaccccctgaa ggcgaagtcg gagtacttgg ttgaggttg cgttgaccgt     600 gttgagcggc aaaagaaggt cttctctgaat gctgccatct atgacaagga cagccatgcc    660
tgcgtgaaag caaaggtgtt gtacatcgtc aaaaagaagt ga                        702

<210> SEQ ID NO 62
<211> LENGTH: 233
<212> TYPE: PRT
<213> ORGANISM: Symbiodinium microadriaticum

<400> SEQUENCE: 62

Met Ala Phe Arg Leu Cys Ser Leu Ser Arg Arg Phe Ala Ala His Ala
1               5                   10                  15

Gln Gln Val Leu Arg Lys Glu Ala Gly Phe Glu Phe Arg Ala Ser Cys
            20                  25                  30

Ile Ala Ile Thr Ala Gly Ile Ser Ala Gly Trp Cys Met Gln Gln Ala
        35                  40                  45

Ala Arg Ala Glu Gly Ile Trp Thr Pro His Leu Gly Glu Glu Ala Lys
    50                  55                  60

Leu Leu Asn Leu Gln Arg Glu Met Ala Leu Arg Asp Arg His Asp Lys
65                  70                  75                  80

Gln Phe Val Trp Gln Thr Cys Ser Gly Gln Gly Lys Ile Glu Asp Cys
                85                  90                  95

Arg Ile Tyr His Cys Lys Arg Glu Glu Val Asp Arg Glu Val Ser Leu
            100                 105                 110
```

```
Asp Ala Pro Glu Met Val Glu Gly Lys Thr Arg Ile Cys Ala Val Met
        115                 120                 125
Arg Val Gly Asp Glu Leu Asn Gly His Pro Gly Leu Leu His Gly Gly
    130                 135                 140
Phe Thr Ala Ala Val Leu Asp Asp Phe Thr Gly Leu Ala Thr Trp Met
145                 150                 155                 160
Glu Lys Gln Ala Gln Ala Leu Asp Lys Asp Ala Ala Ile Phe Thr Ala
                165                 170                 175
His Met Asp Leu Ser Tyr Arg Arg Pro Leu Lys Ala Lys Ser Glu Tyr
            180                 185                 190
Leu Val Glu Val Cys Val Asp Arg Val Glu Arg Gln Lys Lys Val Phe
        195                 200                 205
Leu Asn Ala Ala Ile Tyr Asp Lys Asp Ser His Ala Cys Val Lys Ala
    210                 215                 220
Lys Val Leu Tyr Ile Val Lys Lys Lys
225                 230
```

METHOD OF PRODUCING LIPID

TECHNICAL FIELD

The present invention relates to a method of producing lipids. Further, the present invention also relates to an acyl-CoA synthetase, a gene encoding the same, and a transformant wherein the expression of the gene is enhanced, for use in this method.

BACKGROUND ART

Fatty acids are one of the principal components of lipids. In vivo, fatty acids are bonded to glycerin via an ester bond to form lipids (fats and oils) such as triacylglycerol. Further, many animals and plants also store and utilize fatty acids as an energy source. These fatty acids and lipids stored in animals and plants are widely utilized for food or industrial use.

For example, higher alcohol derivatives that are obtained by reducing higher fatty acids having approximately 12 to 18 carbon atoms are used as surfactants. Alkyl sulfuric acid ester salts, alkyl benzene sulfonic acid salts and the like are utilized as anionic surfactants. Further, polyoxyalkylene alkyl ethers, alkyl polyglycosides and the like are utilized as nonionic surfactants. These surfactants are used for detergents, disinfectants, or the like. Cationic surfactants such as alkylamine salts and mono- or dialkyl-quaternary ammonium salts, as other higher alcohol derivatives, are commonly used for fiber treatment agents, hair conditioning agents, disinfectants, or the like. Further, benzalkonium type quaternary ammonium salts are commonly used for disinfectants, antiseptics, or the like. Furthermore, vegetable fats and oils are also used as raw materials of biodiesel fuels.

Fatty acids and lipids are widely used for various applications shown above, and therefore, it has been attempted to enhance the productivity of fatty acids or lipids in vivo by using plants and the like. Furthermore, the applications and usefulness of fatty acids depend on the number of carbon atoms. Therefore, controlling of the number of carbon atoms of the fatty acids, namely, a chain length thereof has also been attempted.

A fatty acid synthetic pathway of plants is localized in the chloroplast. In the chloroplast, an elongation reaction of the carbon chain is repeated starting from an acetyl-ACP (acyl-carrier-protein), and finally an acyl-ACP (a composite consisting of an acyl group being a fatty acid residue and an ACP. Here, the number of carbon atoms indicates the number of carbon atoms of the acyl group, and indicates the same hereinafter in several cases) having about 18 carbon atoms is synthesized.

The synthesized acyl-ACP is formed into a free fatty acid by an acyl-ACP thioesterase (hereinafter, also simply referred to as "TE"). Then, the free fatty acid is bonded with a CoA according to function of an acyl-CoA synthetase (hereinafter, also simply referred to as "ACS"). Then, the fatty acyl-CoA is incorporated into a glycerol skeleton by various acyltransferases, and is accumulated as the triacylglycerol formed in which three molecules of the fatty acids are ester-bonded with one molecule of glycerol.

It is known that ACS binds free fatty acids and CoA, and is involved not only in synthesis of triacylglycerol but also in the elongation reaction of the fatty acids or a modification reaction such as desaturation, and also in degradation of the fatty acids by β-oxidation. Further, various ACSs are also known to exhibit specificity to the chain length of the fatty acids.

In recent years, researches on renewable energy have been promoted toward realization of a sustainable society. In particular, photosynthetic microorganisms are expected as biofuel organisms without competing with grain in addition to an effect on reducing carbon dioxide.

Especially recently, algae attract attention due to its usefulness in biofuel production. The algae can produce lipids that can be used as the biodiesel fuels through photosynthesis, and do not compete with foods. Therefore, the algae attract attention as next-generation biomass resources. Moreover, it is also reported that the algae have higher lipid productivity and accumulation ability in comparison with plants. Research has started on a lipid synthesis and accumulation mechanism of the algae and lipid production technologies utilizing the mechanism, but unclear parts remain in many respects.

A great number of researches have so far reported on ACS derived from plants, animal cells and yeast. However, only a few studies have reported on ACS derived from microalgae, to the extent to which ACS is obtained from a certain kind of species of organisms (see Non-Patent Literatures 1 to 3) or ACS can be utilized for producing polyunsaturated fatty acids or bio-polyester (see Patent Literatures 1 and 2). Then, an amino acid sequence of a certain kind of ACS is determined from a genome sequence analysis of the microalgae (see Patent Literature 3). However, almost no studies have reported on a technology on producing a medium-chain fatty acid having about 10 to 14 carbon atoms by utilizing ACS.

CITATION LIST

Patent Literatures

Patent Literature 1: WO 2006/037947
Patent Literature 2: WO 02/040690
Patent Literature 3: US 2013/0102040

Non-Patent Literatures

Non-Patent Literature 1: Plant Physiology, 2005, Vol. 138 (1), p. 402-408
Non-Patent Literature 2: J. Appl. Phycol., 2012, Vol. 24, p. 873-880
Non-Patent Literature 3: Plant Physiology and Biochemistry, 2014, Vol. 74, p. 33-41

SUMMARY OF INVENTION

The present invention relates to a method of producing lipids, containing the steps of:
culturing a transformant wherein the expression of a gene encoding any one of the following proteins (A) to (F) is enhanced, and
producing fatty acids or lipids containing these fatty acids as components:
(A) a protein consisting of the amino acid sequence set forth in SEQ ID NO: 2;
(B) a protein consisting of an amino acid sequence having 89% or more identity with the amino acid sequence of the protein (A), and having acyl-CoA synthetase activity;
(C) a protein consisting of the amino acid sequence set forth in SEQ ID NO: 4;
(D) a protein consisting of an amino acid sequence having 49% or more identity with the amino acid sequence of the protein (C), and having acyl-CoA synthetase activity;

(E) a protein consisting of the amino acid sequence set forth in SEQ ID NO: 6; and (F) a protein consisting of an amino acid sequence having 85% or more identity with the amino acid sequence of the protein (E), and having acyl-CoA synthetase activity.

Further, the present invention relates to a method of modifying the composition of lipids, containing the steps of:

enhancing the expression of a gene encoding any one of the proteins (A) to (F) in a transformant, and improving the productivity of medium-chain fatty acids or lipids containing these fatty acids as components produced in a cell of the transformant, to modify the composition of fatty acids or lipids in all fatty acids or all lipids to be produced.

The present invention relates to a transformant, wherein the expression of a gene encoding any one of the proteins (A) to (F) is enhanced.

Further, the present invention relates to the proteins (A) to (F).

Furthermore, the present invention relates to a gene encoding any one of the proteins.

Other and further features and advantages of the invention will appear more fully from the following description.

MODE FOR CARRYING OUT THE INVENTION

The present invention relates to providing a method of producing lipids, which improves productivity of medium-chain fatty acids or lipids containing these fatty acids as components.

Further, the present invention relates to providing a transformant in which the productivity of medium-chain fatty acids or lipids containing these fatty acids as components is improved.

The present inventors newly identified, as enzymes involved in a medium-chain fatty acid synthesis, several kinds of ACSs of algae of the genus Nannochloropsis being one kind of algae. Then, the present inventor enhanced expression of the each ACS in microorganisms, and as the result, found that the productivity of medium-chain fatty acids or lipids containing these fatty acids as components to be produced is significantly improved.

Furthermore, the present inventors found that the productivity of medium-chain fatty acids or lipids containing these fatty acids as component is further improved by enhancing expression of TE in addition to the ACS.

The present invention was completed based on these findings.

According to the method of producing the lipids of the present invention, the productivity of medium-chain fatty acids or lipids containing these fatty acids as components can be improved.

Moreover, the transformant of the present invention is excellent in the productivity of medium-chain fatty acids or lipids containing these fatty acids as components.

The term "lipid(s)" in the present specification, covers a simple lipid such as a neutral lipid (triacylglycerol, or the like), wax, and a ceramide; a complex lipid such as a phospholipid, a glycolipid, and a sulfolipid; and a derived lipid obtained from the lipid such as a fatty acid (free fatty acid), alcohols, and hydrocarbons.

The fatty acids categorized into the derived lipid generally refer to the fatty acids per se and mean "free fatty acids". In the present invention, a part of the fatty acids or a part of the acyl group in molecules of a simple lipid and a complex lipid is expressed as "fatty acid residue". Then, unless otherwise specified, a term "fatty acid" is used as a generic term for "free fatty acid" and "fatty acid residue".

Moreover, a term "fatty acids or lipids containing these fatty acids as components" in the present specification is generically used including "free fatty acids" and "lipids having the fatty acid residues". Further, a term "fatty acid composition" in the present specification means a weight proportion of each fatty acid relative to the weight of whole fatty acids (total fatty acids) obtained by totaling the free fatty acids and the fatty acid residues described above. The weight (production amount) of the fatty acids or the fatty acid composition can be measured according to the method used in Examples.

In the present specification, the description of "Cx:y" for the fatty acid or the acyl group constituting the fatty acid means that the number of carbon atoms is "x" and the number of double bonds is "y". The description of "Cx" means a fatty acid or an acyl group having "x" as the number of carbon atoms.

In the present specification, the identity of the nucleotide sequence and the amino acid sequence is calculated through the Lipman-Pearson method (Science, 1985, vol. 227, p. 1435-1441). Specifically, the identity can be determined through use of a homology analysis (search homology) program of genetic information processing software Genetyx-Win with Unit size to compare (ktup) being set to 2.

It should be note that, in the present specification, the "stringent conditions" includes, for example, the method described in Molecular Cloning—A LABORATORY MANUAL THIRD EDITION [Joseph Sambrook and David W. Russell, Cold Spring Harbor Laboratory Press], and examples thereof include conditions where hybridization is performed by incubating a solution containing 6×SSC (composition of 1×SSC: 0.15 M sodium chloride, 0.015 M sodium citrate, pH 7.0), 0.5% SDS, 5×Denhardt's solution and 100 mg/mL herring sperm DNA together with a probe at 65° C. for 8 to 16 hours.

Furthermore, in the present specification, the term "upstream" of a gene means a region subsequent to a 5' side of a targeted gene or region, and not a position from a translational initiation site. On the other hand, the term "downstream" of the gene means a region subsequent to a 3' side of the targeted gene or region.

The above-described protein (A) or (B) (hereinafter, also referred to as "LACS2"), the above-described protein (C) or (D) (hereinafter, also referred to as "LACS6"), and the above-described protein (E) or (F) (hereinafter, also referred to as "LACS11"), are one of the KAS, and the proteins involved in an acyl-CoA synthesis, by adding a CoA to a fatty acid (free fatty acid) to be synthesized. The protein consisting of the amino acid sequence set forth in SEQ ID NO: 2, the protein consisting of the amino acid sequence set forth in SEQ ID NO: 4, and the protein consisting of the amino acid sequence set forth in SEQ ID NO: 6 all are one of the ACS derived from Nannochloropsis oculata NIES-2145 being algae belonged to the genus Nannochloropsis.

The proteins (A) to (F) described above have the acyl-CoA synthetase activity (hereinafter, also referred to as "ACS activity"). In the present specification, the term "ACS activity" means the activity to bind a free tatty acid and a CoA to synthesize an acyl-CoA.

It can be confirmed that the protein has the ACS activity by a system using an ACS gene deletion strain, for example. Alternatively, it can be confirmed by introducing DNA in which the gene encoding the above-described protein is linked to the downstream of a promoter functioning within a host cell into the ACS synthetic gene deletion strain, culturing the resultant in a minimum salt medium applying the free fatty acid as a single carbon source, and examining capability of growth recovery (whether or not the strain can grow by utilizing (dieting) the free fatty acid in the medium). Alternatively, it can also be confirmed by measuring a decrease of CoA amount by using Ellman's reagent (DTNB), by preparing the ACS protein or cell lysate containing the same to react the resultant material with the reaction solution containing free fatty acids, CoA, ATP, Magnesium Ion, or the like.

By the results of Blast analysis using the amino acid sequence and nucleotide sequence, the proteins (A) to (F) were thought to be one of the ACS.

As shown in Examples mentioned later, the productivity of medium-chain fatty acids having 10 to 14 carbon atoms is improved in the transformant, wherein the expression of the gene encoding each protein (A) to (F) is enhanced. Therefore, all of the proteins (A) to (F) are the ACS which can improve the content of medium-chain fatty acids in the living body.

Note that, in the present specification, the term "medium-chain" means that the number of carbon atoms of the acyl group is 6 or more and 14 or less, preferably 8 or more and 14 or less, more preferably 10 or more and 14 or less, further preferably 10, 12, or 14. The term "long-chain" means that the number of carbon atoms of the acyl group is 15 or more, and preferably 16 or more.

In the protein (B), the identity with the amino acid sequence of the protein (A) is preferably 90% or more, preferably 92% or more, more preferably 93% or more, further preferably 94% or more, further preferably 95% or more, further preferably 96% or more, further preferably 97% or more, further preferably 98% or more, and furthermore preferably 99% or more, in view of ACS activity.

Further, specific examples of the protein (B) include a protein in which 1 or several (for example 1 or more and 71 or less, preferably 1 or more and 64 or less, more preferably 1 or more and 51 or less, further preferably 1 or more and 45 or less, furthermore preferably 1 or more and 38 or less, furthermore preferably 1 or more and 32 or less, furthermore preferably 1 or more and 25 or less, furthermore preferably 1 or more and 19 or less, furthermore preferably 1 or more and 12 or less, and furthermore preferably 1 or more and 6 or less) amino acids are deleted, substituted, inserted or added to the amino acid sequence of the protein (A).

In the protein (D), the identity with the amino acid sequence of the protein (C) is preferably 50% or more, preferably 55% or more, more preferably 60% or more, further preferably 65% or more, further preferably 70% or more, further preferably 75% or more, further preferably 80% or more, further preferably 85% or more, further preferably 90% or more, further preferably 92% or more, further preferably 93% or more, further preferably 94% or more, further preferably 95% or more, further preferably 96% or more, further preferably 97% or more, further preferably 98% or more, and furthermore preferably 99% or more, in view of ACS activity.

Further, specific examples of the protein (D) include a protein in which 1 or several (for example 1 or more and 541 or less, preferably 1 or more and 531 or less, more preferably 1 or more and 477 or less, further preferably 1 or more and 424 or less, furthermore preferably 1 or more and 371 or less, furthermore preferably 1 or more and 318 or less, furthermore preferably 1 or more and 265 or less, furthermore preferably 1 or more and 212 or less, furthermore preferably 1 or more and 159 or less, furthermore preferably 1 or more and 106 or less, furthermore preferably 1 or more and 84 or less, furthermore preferably 1 or more and 74 or less, furthermore preferably 1 or more and 63 or less, furthermore preferably 1 or more and 53 or less, furthermore preferably 1 or more and 42 or less, furthermore preferably 1 or more and 31 or less, furthermore preferably 1 or more and 21 or less, and furthermore preferably 1 or more and 10 or less) amino acids are deleted, substituted, inserted or added to the amino acid sequence of the protein (C).

In the protein (F), the identity with the amino acid sequence of the protein (E) is preferably 90% or more, preferably 92% or more, more preferably 93% or more, further preferably 94% or more, further preferably 95% or more, further preferably 96% or more, further preferably 97% or more, further preferably 98% or more, and furthermore preferably 99% or more, in view of ACS activity.

Further, specific examples of the protein (F) include a protein in which 1 or several (for example 1 or more and 112 or less, preferably 1 or more and 74 or less, more preferably 1 or more and 59 or less, further preferably 1 or more and 52 or less, furthermore preferably 1 or more and 44 or less, furthermore preferably 1 or more and 37 or less, furthermore preferably 1 or more and 29 or less, furthermore preferably 1 or more and 22 or less, furthermore preferably 1 or more and 14 or less, and furthermore preferably 1 or more and 7 or less) amino acids are deleted, substituted, inserted or added to the amino acid sequence of the protein (E).

A method of introducing the mutation into an amino acid sequence includes a method of, for example, introducing a mutation into a nucleotide sequence encoding the amino acid sequence. A method of introducing the mutation includes a method of introducing a site-specific mutation. Specific examples of the method of introducing the site-specific mutation include a method of utilizing the SOE-PCR, the ODA method, and the Kunkel method. Further, commercially available kits such as Site-Directed Mutagenesis System Mutan-Super Express Km kit (Takara Bio), Transformer TM Site-Directed Mutagenesis kit (Clontech Laboratories), and KOD-Plus-Mutagenesis Kit (TOYOBO) can also be utilized. Furthermore, a gene containing a desired mutation can also be obtained by introducing a genetic mutation at random, and then performing an evaluation of the enzyme activities and a gene analysis thereof by an appropriate method.

The proteins (A) to (F) can be obtained by chemical techniques, genetic engineering techniques or the like that are ordinarily carried out. For example, a natural product-derived protein can be obtained through isolation, purification and the like from *Nannochloropsis oculata*. In addition, the proteins (A) to (F) can be obtained by artificial chemical synthesis based on the amino acid sequence set forth in SEQ ID NO: 2, 4, or 6. Alternatively, as recombinant proteins, proteins (A) to (F) may also be produced by gene recombination technologies. In the case of producing the recombinant protein, the ACS gene described below can be used.

Note that the algae such as *Nannochloropsis oculata* can be obtained from culture collection such as private or public research institutes or the like. For example, *Nannochloropsis oculata* strain NIES-2145 can be obtained from National Institute for Environmental Studies (NIES).

An example of the gene encoding any one of the proteins (A) to (F) (hereinafter, also referred to as "ACS gene" or "LACS gene") includes a gene consisting of any one of the following DNAs (a) to (f):

(a) a DNA consisting of the nucleotide sequence set forth in SEQ ID NO: 1;

(b) a DNA consisting of a nucleotide sequence having 70% or more identity with the nucleotide sequence of the DNA (a), and encoding a protein having ACS activity;
(c) a DNA consisting of the nucleotide sequence set forth in SEQ ID NO: 3;
(d) a DNA consisting of a nucleotide sequence having 70% or more identity with the nucleotide sequence of the DNA (c), and encoding a protein having ACS activity;
(e) a DNA consisting of the nucleotide sequence set forth in SEQ ID NO: 5; and
(f) a DNA consisting of a nucleotide sequence having 70% or more identity with the nucleotide sequence of the DNA (e), and encoding a protein having ACS activity.

The nucleotide sequence set forth in SEQ ID NO: 1 is a nucleotide sequence of a gene encoding a protein (hereinafter, also referred to as "LACS2 gene") consisting of the amino acid sequence set forth in SEQ ID NO: 2.

The nucleotide sequence set forth in SEQ ID NO: 3 is a nucleotide sequence of a gene encoding a protein (hereinafter, also referred to as "LACS6 gene") consisting of the amino acid sequence set forth in SEQ ID NO: 4.

The nucleotide sequence set forth in SEQ ID NO: 5 is a nucleotide sequence of a gene encoding a protein (hereinafter, also referred to as "LACS11 gene") consisting of the amino acid sequence set forth in SEQ ID NO: 6.

In the DNA (b), the identity with the nucleotide sequence of the DNA (a) is preferably 75% or more, more preferably 80% or more, further preferably 85% or more, further preferably 90% or more, further preferably 92% or more, further preferably 93% or more, further preferably 94% or more, further preferably 95% or more, further preferably 96% or more, further preferably 97% or more, further preferably 98% or more, and furthermore preferably 99% or more, in view of ACS activity.

Further, the DNA (b) is also preferably a DNA in which 1 or several (for example 1 or more and 584 or less, preferably 1 or more and 486 or less, more preferably 1 or more and 389 or less, further preferably 1 or more and 292 or less, furthermore preferably 1 or more and 194 or less, furthermore preferably 1 or more and 155 or less, furthermore preferably 1 or more and 136 or less, furthermore preferably 1 or more and 116 or less, furthermore preferably 1 or more and 97 or less, furthermore preferably 1 or more and 77 or less, furthermore preferably 1 or more and 58 or less, furthermore preferably 1 or more and 38 or less, and furthermore preferably 1 or more and 19 or less) nucleotides are deleted, substituted, inserted or added to the nucleotide sequence of the DNA (a), and encoding the protein (A) or (B) having ACS activity.

Furthermore, the DNA (b) is also preferably a DNA capable of hybridizing with a DNA consisting of a nucleotide sequence complementary with the DNA (a) under a stringent condition, and encoding the protein (A) or (B) having ACS activity.

In the DNA (d), the identity with the nucleotide sequence of the DNA (c) is preferably 75% or more, more preferably 80% or more, further preferably 85% or more, further preferably 90% or more, further preferably 92% or more, further preferably 93% or more, further preferably 94% or more, further preferably 95% or more, further preferably 96% or more, further preferably 97% or more, further preferably 98% or more, and furthermore preferably 99% or more, in view of ACS activity.

Further, the DNA (d) is also preferably a DNA in which 1 or several (for example 1 or more and 956 or less, preferably 1 or more and 797 or less, more preferably 1 or more and 637 or less, further preferably 1 or more and 478 or less, furthermore preferably 1 or more and 318 or less, furthermore preferably 1 or more and 255 or less, furthermore preferably 1 or more and 223 or less, furthermore preferably 1 or more and 191 or less, furthermore preferably 1 or more and 159 or less, furthermore preferably 1 or more and 127 or less, furthermore preferably 1 or more and 95 or less, furthermore preferably 1 or more and 63 or less, and furthermore preferably 1 or more and 31 or less) nucleotides are deleted, substituted, inserted or added to the nucleotide sequence of the DNA (c), and encoding the protein (C) or (D) having ACS activity.

Furthermore, the DNA (d) is also preferably a DNA capable of hybridizing with a DNA consisting of a nucleotide sequence complementary with the DNA (c) under a stringent condition, and encoding the protein (C) or (D) having ACS activity.

In the DNA (f), the identity with the nucleotide sequence of the DNA (e) is preferably 75% or more, more preferably 80% or more, further preferably 85% or more, further preferably 90% or more, further preferably 92% or more, further preferably 93% or more, further preferably 94% or more, further preferably 95% or more, further preferably 96% or more, further preferably 97% or more, further preferably 98% or more, and furthermore preferably 99% or more, in view of ACS activity.

Further, the DNA (f) is also preferably a DNA in which 1 or several (for example 1 or more and 674 or less, preferably 1 or more and 561 or less, more preferably 1 or more and 449 or less, further preferably 1 or more and 337 or less, furthermore preferably 1 or more and 224 or less, furthermore preferably 1 or more and 179 or less, furthermore preferably 1 or more and 157 or less, furthermore preferably 1 or more and 134 or less, furthermore preferably 1 or more and 112 or less, furthermore preferably 1 or more and 89 or less, furthermore preferably 1 or more and 67 or less, furthermore preferably 1 or more and 44 or less, and furthermore preferably 1 or more and 22 or less) nucleotides are deleted, substituted, inserted or added to the nucleotide sequence of the DNA (e), and encoding the protein (E) or (F) having ACS activity.

Furthermore, the DNA (f) is also preferably a DNA capable of hybridizing with a DNA consisting of a nucleotide sequence complementary with the DNA (e) under a stringent condition, and encoding the protein (E) or (F) having ACS activity.

A method of enhancing the expression of the ACS gene can be appropriately selected from an ordinarily method. For example, a method of introducing the ACS gene into a host, or a method of modifying expression regulation regions of the gene (promoter, terminator, or the like) in a host having the ACS gene on a genome, can be selected. Among them, the method of introducing the ACS gene into a host to enhance the expression of the ACS gene is preferred.

Hereinafter, in the present specification, a cell in which expression of a gene (ACS gene) encoding a target protein (ACS) is enhanced is also referred to as the "transformant", and a cell in which the expression of the gene encoding the target protein is not enhanced is also referred to as the "host" or "wild type strain".

In the transformant used in the present invention, the productivity of medium-chain fatty acids and lipids containing these medium-chain fatty acids as components, particularly a proportion of medium-chain fatty acids and lipids containing these medium-chain fatty acids as components in the whole fatty acids or lipids to be produced is significantly improved, in comparison with a host. Moreover, as a result, in the transformant, the fatty acid composition in the lipid is modified. Therefore, the present invention using the transformant can be preferably applied to production of lipids having specific number of carbon atoms, particularly medium-chain fatty acids and lipids containing these medium-chain fatty acids as components, preferably fatty acids having 6 to 14 carbon atoms and lipids containing these fatty acids as components, more preferably fatty acids having 8 to 14 carbon atoms and lipids containing these fatty acids as components, further preferably fatty acids having 10 to 14 carbon atoms and lipids containing these fatty acids as components, further preferably fatty acids having 10, 12 or 14 carbon atoms and lipids containing these fatty acids as components, further preferably saturated fatty acids having 10, 12 or 14 carbon atoms (capric acid, lauric acid, or myristic acid) and lipids containing these fatty acids as components.

The productivity of fatty acids and lipids of the host and the transformant can be measured by the method used in Examples described below.

The method of introducing the ACS gene into a host to enhance the expression of the gene is described.

The ACS gene can be obtained by genetic engineering techniques that are ordinarily carried out. For example, the ACS gene can be artificially synthesized based on the amino acid sequence set forth in SEQ ID NO: 2, 4, or 6, or the nucleotide sequence set forth in SEQ ID NO: 1, 3, or 5. The synthesis of the ACS gene can be achieved by utilizing, for example, the services of Invitrogen. Further, the gene can also be obtained by cloning from *Nannochloropsis oculata*. The cloning can be carried out by, for example, the methods described in Molecular Cloning: A LABORATORY MANUAL THIRD EDITION [Joseph Sambrook, David W. Russell, Cold Spring Harbor Laboratory Press (2001)]. Furthermore, *Nannochloropsis oculata* NIES-2145 used in Examples can be obtained from National Institute for Environmental Studies (NIES).

The transformant that can be preferably used in the present invention is obtained by introducing the ACS gene into a host according to an ordinarily method. Specifically, the transformant can be produced by preparing a recombinant vector or a gene expression cassette which is capable of expressing the ACS gene in a host cell, introducing this vector or cassette into the host cell, and thereby transforming the host cell.

The host for the transformant can be appropriately selected from ordinarily used hosts. For example, microorganisms (including algae and microalgae), plants or animals can be used as the host in the present invention. Among these, microorganisms or plants are preferable, microorganisms are more preferable, and microalgae are further preferable as a host, from the viewpoints of production efficiency and the usability of lipids to be obtained.

As the microorganisms, prokaryotes and eukaryotes can be used. Examples of the prokaryotes include microorganisms belonging to the genus *Escherichia*, microorganisms belonging to the genus *Bacillus*, microorganisms belonging to the genus *Synechocystis*, microorganisms belonging to the genus *Synechococcus*, and the like. Examples of the eukaryotes include eukaryotic microorganisms belonging to yeast, filamentous fungi and the like. Among these, from a viewpoint of the lipid productivity, *Escherichia coli*, *Bacillus subtilis*, *Rhodosporidium toruloides*, or *Mortierella* sp., is preferable, and *Escherichia coli* is more preferable.

As the algae or microalgae, from a viewpoint of establishment of a gene recombination technique, algae belonging to the genus *Chlamydomonas*, algae belonging to the genus *Chlorella*, algae belonging to the genus *Phaeodactylum*, or algae belonging to the genus *Nannochloropsis* are preferable, and algae belonging to the genus *Nannochloropsis* are more preferable. Specific examples of the algae belonging to the genus *Nannochloropsis* include *Nannochloropsis oculata*, *Nannochloropsis gaditana*, *Nannochloropsis salina*, *Nannochloropsis oceanica*, *Nannochloropsis atomus*, *Nannochloropsis maculata*, *Nannochloropsis granulata*, *Nannochloropsis* sp., and the like. Among these, from a viewpoint of the lipid productivity, *Nannochloropsis oculata* or *Nannochloropsis gaditana* is preferable, and *Nannochloropsis oculata* is more preferable.

As the plants, from a viewpoint of a high lipid content of seeds, *Arabidopsis thaliana*, *Brassica napus*, *Brassica raga*, *Cocos nucifera*, *Elaeis quineensis*, *cuphea*, *Glycine max*, *Zea mays*, *Oryza sativa*, *Helianthus annuus*, *Cinnamomum camphora*, or *Jatropha curcas* is preferable, and *Arabidopsis thaliana* is more preferable.

A vector for use as the plasmid vector for gene expression or a vector containing the gene expression cassette (plasmid) may be any vector capable of introducing the gene encoding the target protein into a host, and expressing the gene in the host cell. For example, a vector which has expression regulation regions such as a promoter and a terminator in accordance with the type of the host to be introduced, and has a replication initiation point, a selection marker or the like, can be used. Furthermore, the vector may also be a vector such as a plasmid capable of self-proliferation and self-replication outside the chromosome, or may also be a vector which is incorporated into the chromosome.

Specific examples of the vector that can be used preferably in the present invention include, in the case of using a microorganism as the host, pBluescript (pBS) II SK(−) (manufactured by Stratagene), a pSTV-based vector (manufactured by Takara Bio), a pUC-based vector (manufactured by Takara Shuzo), a pET-based vector (manufactured by Takara Bio), a pGEX-based vector (manufactured by GE Healthcare), a pCold-based vector (manufactured by Takara Bio), pHY300PLK (manufactured by Takara Bio), pUB110 (McKenzie, T. et al., 1986, Plasmid 15(2), p. 93-103), pBR322 (manufactured by Takara Bio), pRS403 (manufactured by Stratagene), and pMW218/219 (manufactured by Nippon Gene). In particular, in the case of using *Escherichia coli* as the host, pBluescript II SK(−) or pMW218/219 is preferably used.

When the algae or the microalgae are used as the host, specific examples of the vector include pUC19 (manufactured by Takara Bio), P66 (*Chlamydomonas* Center), P-322 (*Chlamydomonas* Center), pPha-T1 (see Yangmin Gong, et al., Journal of Basic Microbiology, 2011, vol. 51, p. 666-672) and pJET1 (manufactured by COSMO BIO). In particular, in the case of using the algae belonging to the genus *Nannochloropsis* as the host, pUC19, pPha-T1 or pJET1 is preferably used. Moreover, when the host is the algae belonging to the genus *Nannochloropsis*, the host can be transformed, with referring to the method described in Oliver Kilian, et al., Proceedings of the National Academy of Sciences of the United States of America, 2011, vol. 108(52), by using the DNA fragment consisting of the target gene of the present invention, a promoter and a terminator (gene expression cassette). Specific examples of this DNA fragment include a DNA fragment amplified by PCR method, and a restriction enzyme-cut DNA fragment.

In the case of using a plant cell as the host, examples of the vector include a pRI-based vector (manufactured by Takara Bio), a pBI-based vector (manufactured by Clontech), and an IN3-based vector (manufactured by Inplanta Innovations). In particular, in the case of using *Arabidopsis thaliana* as the host, a pRI-based vector or a pBI-based vector is preferably used.

Moreover, a kind of promoter regulating the expression of the gene encoding a target protein, which is introduced into the expression vector, can also be appropriately selected according to a kind of the host to be used. Specific examples of the promoter that can be preferably used in the present invention include lac promoter, trp promoter, tac promoter, trc promoter, T7 promoter, SpoVG promoter, a promoter that relates to a substance that can be induced by addition of isopropyl β-D-1-thiogalactopyranoside (IPTG), Rubisco operon (rbc), PSI reaction center protein (psaAB), D1 protein of PSII (psbA), c-phycocyanin β subunit (cpcB), cauliflower mosaic virus 35S RNA promoter, promoters for housekeeping genes (e.g., tubulin promoter, actin promoter and ubiquitin promoter), *Brassica napes* or *Brassica rapa*-derived Napin gene promoter, plant-derived Rubisco promoter, a promoter of a violaxanthin/(chlorophyll a)-binding protein gene derived from the genus *Nannochloropsis* (VCP1 promoter, VCP2 promoter) (Oliver Kilian, et al., Proceedings of the National Academy of Sciences of the United States of America, 2011, vol. 108(52)), and a promoter of an oleosin-like protein LDSP (lipid droplet surface protein) gene derived from the genus *Nannochloropsis* (Astrid Vieler, et al., PLOS Genetics, 2012, vol. 8(11): e1003064. DOI: 10.1371). In the case of using *Nannochloropsis* as the host in the present invention, the promoter of violaxanthin/(chlorophyll a)-binding protein gene, or the promoter of an oleosin-like protein LDSP gene derived from the genus *Nannochloropsis* can be preferably used.

Moreover, a kind of selection marker for confirming introduction of the gene encoding a target protein can also be appropriately selected according to a kind of the host to be used. Examples of the selection marker that can be preferably used in the present invention include drug resistance genes such as an ampicillin resistance gene, a chloramphenicol resistance gene, an erythromycin resistance gene, a neomycin resistance gene, a kanamycin resistance gene, a spectinomycin resistance gene, a tetracycline resistance gene, a blasticidin S resistance gene, a bialaphos resistance gene, a zeocin resistance gene, a paromomycin resistance gene, a gentamicin resistance gene, and a hygromycin resistance gene. Further, it is also possible to use a deletion of an auxotrophy-related gene or the like as the selection marker gene.

Introduction of the gene encoding a target protein to the vector can be conducted by an ordinary technique such as restriction enzyme treatment and ligation.

Furthermore, the method for transformation can be appropriately selected from ordinary techniques according to a kind of the host to be used. Examples of the method for transformation include a transformation method of using calcium ion, a general competent cell transformation method, a protoplast transformation method, an electroporation method, an LP transformation method, a method of using *Agrobacterium*, a particle gun method, and the like. When the algae belonging to the genus *Nannochloropsis* are used as the host, transformation can also be performed by using the electroporation method described in Randor Radakovits, et al., Nature Communications, DOI: 10.1038/ncomms1688, 2012, or the like.

The selection of a transformant having a target gene fragment introduced therein can be carried out by utilizing the selection marker or the like. For example, the selection can be carried out by using an indicator whether a transformant acquires the drug resistance as a result of introducing a drug resistance gene into a host cell together with a target DNA fragment upon the transformation. Further, the introduction of a target DNA fragment can also be confirmed by PCR method using a genome as a template or the like.

In a host having the ACS gene on a genome, a method of modifying expression regulation regions of the gene and enhancing the expression of the gene is described.

The "expression regulation region" indicates the promoter or the terminator, in which these sequences are generally involved in regulation of the expression amount (transcription amount, translation amount) of the gene adjacent thereto. In a host having the above-described ACS gene on a genome, productivity of medium-chain fatty acids or lipids containing these medium-chain fatty acids as components can be improved by modifying expression regulation regions of the gene and enhancing the expression of the ACS gene.

Specific examples of the method of modifying the expression regulation regions include interchange of promoters. In the host having the above-mentioned ACS gene on the genome, the expression of the above-described ACS gene can be enhanced by interchanging the promoter of the gene (hereinafter, also referred to as "ACS promoter") with a promoter having higher transcriptional activity.

For example, in *Nannochloropsis oculata* strain NIES-2145 being one of the hosts having the ACS genes on the genome, the LACS2 gene exists at the downstream of a DNA sequence consisting of the nucleotide sequence set forth in SEQ ID NO: 52, and a promoter region exists in the DNA sequence consisting of the nucleotide sequence set forth in SEQ ID NO: 52. Further, the LACS6 gene exists at the downstream of a DNA sequence consisting of the nucleotide sequence set forth in SEQ ID NO: 53, and a promoter region exists in the DNA sequence consisting of the nucleotide sequence set forth in SEQ ID NO: 53. Furthermore, the LACS11 gene exists at the downstream of a DNA sequence consisting of the nucleotide sequence set forth in SEQ ID NO: 54, and a promoter region exists in the DNA sequence consisting of the nucleotide sequence set forth in SEQ ID NO: 54. Therefore, the expression of the above-described ACS gene can be enhanced by partially or wholly interchanging the DNA sequences consisting of any one of the nucleotide sequences set forth in SEQ ID NO: 52 to 54 with the promoter having higher transcriptional activity.

The promoter used for interchanging the ACS promoter is not particularly limited, and can be appropriately selected from the promoters that are higher in the transcriptional activity than the ACS promoter and suitable for production of the medium-chain fatty acids or the lipids containing these fatty acids as the components.

When the *Nannochloropsis* is used as a host, a tubulin promoter, a heat shock protein promoter, the above-described promoter of a violaxanthin/(chlorophyll a)-binding protein gene (VCP1 promoter, VCP2 promoter), or a promoter of an oleosin-like protein LDSP gene derived from the genus *Nannochloropsis*, can be preferably used. From a viewpoint of improvement in the productivity of medium-chain fatty acids or lipids containing these medium-chain fatty acids as components, the promoter of a violaxanthin/(chlorophyll a)-binding protein gene or the promoter of LDSP gene is more preferable.

The above-described modification of a promoter can employ according to an ordinarily method such as homologous recombination. Specifically, a linear DNA fragment containing upstream and downstream regions of a target promoter and containing other promoter instead of the target promoter is constructed, and the resultant DNA fragment is incorporated into a host cell to cause double crossover homologous recombination on the side upstream and downstream of the target promoter of the host genome. As a result, the target promoter on the genome is substituted with other promoter fragment, and the promoter can be modified.

The method of modifying a target promoter according to such homologous recombination can be conducted with, for example, referring to literature such as Besher et al., Methods in molecular biology, 1995, vol. 47, p. 291-302. In particular, in the case where the host is the algae belonging to the genus *Nannochloropsis*, specific region in a genome can be modified, with referring to literature such as Oliver Kilian, et al., Proceedings of the National Academy of Sciences of the United States of America, 2011, vol. 108 (52), by homologous recombination method.

The transformant of the present invention preferably has enhancing expression of a gene encoding a TE (hereinafter, also referred to as "TE gene"), in addition to the gene encoding any one of the proteins (A) to (F).

As described above, TE is an enzyme that hydrolyzes the thioester bond of the acyl-ACP synthesized by a fatty acid synthase such as the β-ketoacyl-ACP synthase (hereinafter, also referred to as "KAS") to produce a free fatty acid. The function of the TE terminates the fatty acid synthesis on the ACP, and then the thus-hydrolyzed fatty acid is supplied to the synthesis of polyunsaturated fatty acid or triacylglycerol or the like.

Therefore, lipid productivity of the transformant to be used for the lipid production, particularly productivity of the fatty acids can be further improved by enhancing the expression of the TE gene, in addition to the ACS gene.

The TE that can be used in the present invention merely needs to be the protein having acyl-ACP thioesterase activity (hereinafter, also referred to as "TE activity"). Herein, the term "TE activity" means an activity of hydrolyzing the thioester bond of the acyl-ACP.

To date, several TEs having different reaction specificities depending on the number of carbon atoms and the number of unsaturated bonds of the acyl group (fatty acid residue) constituting the acyl-ACP substrate are identified. Therefore, TE is considered to be an important factor in determining the fatty acid composition of an organism. In particular, when a host originally having no gene encoding a TE is used in the transformation, it is preferable to enhance the expression of the gene encoding a TE. In addition, according to enhancing the expression of the TE gene having substrate specificity to the medium-chain acyl-ACP, the productivity of medium-chain fatty acids is improved. The productivity of medium-chain fatty acids is further improved by introducing such a gene.

The TE that can be used in the present invention can be appropriately selected from ordinary TEs and proteins functionally equivalent to the TEs, according to a kind of host or the like.

Specific examples thereof include TE derived from *Cuphea calophylla* subsp. *mesostemon* (GenBank ABB71581); TE derived from *Cinnamomum camphora* (GenBank AAC49151.1); TE derived from *Myristica fragrans* (GenBank AAB71729); TE derived from *Myristica fragrans* (GenBank AAB71730); TE derived from *Cuphea lanceolata* (GenBank CAA54060); TE derived from *Cuphea hookeriana* (GenBank Q39513); TE derived from *Ulumus americana* (GenBank AAB71731); TE derived from *Sorghum bicolor* (GenBank EER87824); TE derived from *Sorghum bicolor* (GenBank EER88593); TE derived from *Cocos nucifera* (CnFatB1: see Jing et al. BMC Biochemistry 2011, 12:44); TE derived from *Cocos nucifera* (CnFatB2: see Jing et al., BMC Biochemistry, 2011, 12:44); TE derived from *Cuphea viscosissima* (CvFatB1: see Jing et al., BMC Biochemistry, 2011, 12:44); TE derived from *Cuphea viscosissima* (CvFatB2: see Jing et al., BMC Biochemistry, 2011, 12:44); TE derived from *Cuphea viscosissima* (CvFatB3: see Jing et al., BMC Biochemistry, 2011, 12:44); TE derived from *Elaeis guineensis* (GenBank AAD42220); TE derived from *Desulfovibrio vulgaris* (GenBank ACL08376); TE derived from *Bacteroides fragilis* (GenBank CAH09236); TE derived from *Parabacteriodes distasonis* (GenBank ABR43801); TE derived from *Bacteroides thetaiotaomicron* (GenBank AAO77182); TE derived from *Clostridium asparagiforme* (GenBank EEG55387); TE derived from *Bryanthella formatexigens* (GenBank EET61113); TE derived from *Geobacillus* sp. (GenBank EDV77528); TE derived from *Streptococcus dysgalactiae* (GenBank BAH81730); TE derived from *Lactobacillus brevis* (GenBank ABJ63754); TE derived from *Lactobacillus plantarum* (GenBank CAD63310); TE derived from *Anaerococcus tetradius* (GenBank EEI82564); TE derived from *Bdellovibrio bacteriovorus* (GenBank CAE80300); TE derived from *Clostridium thermocellum* (GenBank ABN54268); TE derived from *Cocos nucifera* (SEQ ID NO: 56, nucleotide sequence of a gene encoding thereof; SEQ ID NO: 55); TE derived from *Nannochloropsis oculata* (hereinafter, also referred to as "NoTE") (SEQ ID NO: 33, nucleotide sequence of a gene encoding thereof; SEQ ID NO: 32); TE derived from *Umbellularia californica* (hereinafter, also referred to as "BTE") (GenBank AAA34215.1, SEQ ID NO: 47, nucleotide sequence of a gene encoding thereof; SEQ ID NO: 46); TE derived from *Nannochloropsis gaditana* (SEQ ID NO: 58, nucleotide sequence of a gene encoding thereof; SEQ ID NO: 57); TE derived from *Nannochloropsis granulata* (SEQ ID NO: 60, nucleotide sequence of a gene encoding thereof; SEQ ID NO: 59); and TE derived from *Symbiodinium microadriaticum* (SEQ ID NO: 62, nucleotide sequence of a gene encoding thereof; SEQ ID NO: 61).

Moreover, as the proteins functionally equivalent to them, a protein consisting of an amino acid sequence having 50% or more (preferably 70% or more, more preferably 80% or more, and further preferably 90% or more) identity with the amino acid sequence of any one of the TEs described above, and having TE activity, can be also used.

Among these TEs described above, from a viewpoint of the substrate specificity for medium-chain acyl-ACP, TE derived from *Cocos nucifera* (SEQ ID NO: 56, nucleotide sequence of a gene encoding thereof; SEQ ID NO: 55), NoTE (SEQ ID NO: 33, nucleotide sequence of a gene encoding thereof; SEQ ID NO: 32), BTE (SEQ ID NO: 47, nucleotide sequence of a gene encoding thereof; SEQ ID NO: 46), TE derived from *Nannochloropsis gaditana* (SEQ ID NO: 58, nucleotide sequence of a gene encoding thereof; SEQ ID NO: 57), TE derived from *Nannochloropsis granulata* (SEQ ID NO: 60, nucleotide sequence of a gene encoding thereof; SEQ ID NO: 59), TE derived from *Symbiodinium microadriaticum* (SEQ ID NO: 62, nucleotide sequence of a gene encoding thereof; SEQ ID NO: 61), or a protein consisting of an amino acid sequence having 50% or more (preferably 70% or more, more preferably 80% or more, and further preferably 90% or more) identity with the amino acid sequence of these TEs, and having TE activity for medium-chain acyl-ACP (for example, a protein which is encoded by the DNA consisting of the nucleotide sequence set forth in SEQ ID NO: 38) is preferable.

The sequence information or the like of these TEs and the genes encoding thereof can be obtained from, for example, National Center for Biotechnology Information, NCBI, or the like.

The TE activity of the protein can be confirmed by, for example, introducing a DNA produced by linking the TE gene to the downstream of a promoter which functions in a host cell such as *Escherichia coli*, into a host cell which lacks a fatty acid degradation system, culturing the thus-obtained cell under the conditions suitable for the expression of the introduced TE gene, and analyzing any change caused thereby in the fatty acid composition of the host cell or the cultured liquid by using a gas chromatographic analysis or the like.

Alternatively, the TE activity can be measured by introducing a DNA produced by linking the TE gene to the downstream of a promoter which functions in a host cell such as *Escherichia coli*, into a host cell, culturing the thus-obtained cell under the conditions suitable for the expression of the introduced TE gene, and subjecting a disruption liquid of the cell to a reaction which uses acyl-ACPs, as substrates, prepared according to the method of Yuan et al. (Yuan L. et al., Proc. Natl. Acad. Sci. U.S.A., 1995, vol. 92 (23), p. 10639-10643).

The transformants in which expression of the TE gene is enhanced can be prepared by an ordinary method. For example, the transformants can be prepared by a method similar to the above-mentioned method for enhancing expression of the ACS gene, such as a method of introducing the TE gene into a host, or a method of modifying expression regulation regions of a gene in a host having the TE gene on a genome.

Furthermore, in the transformant of the present invention, expression of a gene encoding a KAS or the like, in addition to the above-described gene encoding any one of the proteins (A) to (F), is also preferably enhanced. For example, KAS IV being one of the KAS mainly catalyzes the elongation reaction that the acyl-ACP having 6 carbon atoms is converted to the acyl-ACP having 14 carbon atoms, to synthesize a medium-chain acyl-ACP. Therefore, productivity of medium-chain fatty acids can be further improved by enhancing the expression of the gene encoding the KAS IV in addition to the ACS gene.

The KAS, which can be used in the present invention, can be appropriately selected from the normal KAS, or proteins functionally equivalent to the KAS, according to a kind of host or the like.

Further, the transformants in which the expression of the gene is enhanced can be prepared by an ordinary method. For example, the transformants can be prepared by a method similar to the above-described method for enhancing the expression of the ACS gene, such as a method for introducing a gene encoding the KAS into a host, a method for modifying expression regulation regions of a gene in the host having the gene encoding the KAS on a genome, or the like.

In the transformant of the present invention, productivity of medium-chain fatty acids or lipids containing these fatty acids as components is improved in comparison with the host in which the expression of the gene encoding any one of the proteins (A) to (F) is not enhanced. Accordingly, if the transformant of the present invention is cultured under suitable conditions and then the medium-chain fatty acids or the lipids containing these fatty acids as components are collected from an obtained cultured product or an obtained growth product, the medium-chain fatty acids or the lipids containing these fatty acids as components can be efficiently produced.

Herein, the term "cultured product" means liquid medium and a transformant subjected to cultivation, and the term "growth product" means a transformant subjected to growth.

The culture condition of the transformant of the present invention can be appropriately selected in accordance with the type of the host, and any ordinary used culture condition for the host can be employed. Further, from a viewpoint of the production efficiency of fatty acids, for example, precursor substances involved in the fatty acid biosynthesis system, such as glycerol, acetic acid or glucose, may be added to the medium.

For example, in the case of using *Escherichia coli* as the host, culturing of *Escherichia coli* may be carried out in LB medium or Overnight Express Instant TB Medium (Novagen) at 30° C. to 37° C. for half a day to 1 day.

In the case of using *Arabidopsis thaliana* as the host, for example, growth of *Arabidopsis thaliana* may be carried out at soil under the temperature conditions of 20° C. to 25° C., by continuously irradiating white light or under light illumination conditions of a light period of 16 hours and a dark period of 8 hours, for one to two months.

In the case of using algae as the host, medium based on natural seawater or artificial seawater may be used. Alternatively, commercially available culture medium may also be used. Specific examples of the culture medium include f/2 medium, ESM medium, Daigo's IMK medium, L1 medium and MNK medium. Above all, from viewpoints of an improvement in the lipid productivity and a nutritional ingredient concentration, f/2 medium, ESM medium or Daigo's IMK medium is preferred, f/2 medium or Daigo's IMK medium is more preferred, and f/2 medium is further preferred. For growth promotion of the algae and an improvement in productivity of fatty acids, a nitrogen source, a phosphorus source, metal salts, vitamins, trace metals or the like can be appropriately added to the culture medium.

An amount of the transformant to be seeded to the culture medium is appropriately selected. In view of viability, the amount is preferably 1% (vol/vol) or more, per culture medium. The upper limit thereof is preferably 50% (vol/vol) or less, and more preferably 10% (vol/vol) or less. The range of an amount of the transformant to be seeded is preferably 1 to 50% (vol/vol), and more preferably 1 to 10% (vol/vol), per culture medium. Culture temperature is not particularly limited within the range in which the temperature does not adversely affect growth of the algae, and is ordinarily in the range of 5 to 40° C. From viewpoints of the growth promotion of the algae, the improvement in productivity of fatty acids, and reduction of production cost, the temperature is preferably 10° C. or more, and more preferably 15° C. or more. The upper limit thereof is preferably 35° C. or less, and more preferably 30° C. or less. The range of the culture temperature is preferably 10 to 35° C., and more preferably 15 to 30° C.

Moreover, the algae are preferably cultured under irradiation with light so that photosynthesis can be made. The light irradiation only needs to be made under conditions in which the photosynthesis can be made, and artificial light or sunlight may be applied. From viewpoints of the growth promotion of the algae and the improvement in the productivity of fatty acids, irradiance during the light irradiation is preferably 100 lx or more, more preferably 300 lx or more, and further preferably 1,000 lx or more. The upper limit thereof is preferably 50,000 lx or less, more preferably 10,000 lx or less, and further preferably 6,000 lx or less. The range of irradiance during the light irradiation is preferably 100 to 50,000 lx, more preferably 300 to 10,000 lx, and further preferably 1,000 to 6,000 lx. Moreover, an interval of the light irradiation is not particularly limited. From the viewpoints in a manner similar to the viewpoints described above, the irradiation is preferably performed under a light and dark cycle. In 24 hours, a light period is preferably 8 hours or more, and 10 hours or more. The upper limit thereof is preferably 24 hours or less, and 18 hours or less. The range of the light period is preferably from 8 to 24 hours, more preferably from 10 to 18 hours, and further preferably 12 hours.

Moreover, the algae are preferably cultured in the presence of a carbon dioxide-containing gas or in a culture medium containing carbonate such as sodium hydrogen carbonate so that the photosynthesis can be made. A concentration of carbon dioxide in the gas is not particularly limited. From viewpoints of the growth promotion and the improvement in the productivity of fatty acids, the concentration is preferably 0.03% (which is the same degree as the concentration under atmospheric conditions) or more, more preferably 0.05% or more, further preferably 0.1% or more, and furthermore preferably 0.3% or more. The upper limit thereof is preferably 10% or less, more preferably 5% or less, further preferably 3% or less, and furthermore preferably 1% or less. The range of the concentration of carbon dioxide is preferably from 0.03 to 10%, more preferably from 0.05 to 5%, further preferably from 0.1 to 3%, and furthermore preferably from 0.3 to 1%. A concentration of a carbonate is not particularly limited. When sodium hydrogen carbonate is used, for example, from viewpoints of the growth promotion and the improvement in the productivity of fatty acids, the concentration is preferably 0.01% by mass or more, more preferably 0.05% by mass or more, and further preferably 0.1% by mass or more. The upper limit thereof is preferably 5% by mass or less, more preferably 2% by mass or less, and further preferably 1% by mass or less. The range of the concentration of sodium hydrogen carbonate is preferably from 0.01 to 5% by mass, more preferably from 0.05 to 2% by mass, and further preferably from 0.1 to 1% by mass.

A culture time is not particularly limited, and the culture may be performed for a long time (for example, about 150 days) so that an alga body in which the lipids are accumulated at a high concentration can grow at a high concentration. The culture time is preferably 3 days or more, and more preferably 7 days or more. The upper limit thereof is preferably 90 days or less, and more preferably 30 days or less. The range of the culture time is preferably from 3 to 90 days, more preferably from 3 to 30 days, and further preferably from 7 to 30 days. The culture may be performed in any of aerated and agitated culture, shaking culture or static culture. From a viewpoint of improving air-permeability, shaking culture is preferred.

A method of collecting the lipids from the cultured product or growth product is appropriately selected from an ordinary method. For example, lipid components can be isolated and collected from the above-described cultured product or growth product by means of filtration, centrifugation, cell disruption, gel filtration chromatography, ion exchange chromatography, chloroform/methanol extraction, hexane extraction, ethanol extraction, or the like. In the case of carrying out the larger scales culturing, lipids can be obtained by collecting oil components from the cultured product or growth product through pressing or extraction, and then performing general purification processes such as degumming, deacidification, decoloration, dewaxing, and deodorization. After lipid components are isolated as such, the isolated lipids are hydrolyzed, and thereby fatty acids can be obtained. Specific examples of the method of isolating fatty acids from lipid components include a method of treating the lipid components at a high temperature of about 70° C. in an alkaline solution, a method of performing a lipase treatment, and a method of degrading the lipid components using high-pressure hot water.

The lipids produced in the production method of the present invention preferably contain fatty acids or fatty acid compounds, and more preferably contain fatty acids or fatty acid ester compounds, in view of usability thereof.

In view of usability for a surfactant or the like, the fatty acid or the fatty acid ester compound thereof contained in the lipid is preferably a medium-chain fatty acid or a fatty acid ester compound thereof, more preferably a fatty acid having 6 or more and 14 or less carbon atoms or a fatty acid ester compound thereof, more preferably a fatty acid having 8 or more and 14 or less carbon atoms or a fatty acid ester compound thereof, more preferably a fatty acid having 10 or more and 14 or less carbon atoms or a fatty acid ester compound thereof, more preferably a fatty acid having 10, 12, or 14 carbon atoms or a fatty acid ester compound thereof, more preferably a saturated fatty acid having 10, 12, or 14 carbon atoms (capric acid, lauric acid, or myristic acid) or a fatty acid ester compound thereof.

From a viewpoint of the productivity, the fatty acid ester compound is preferably a simple lipid or a complex lipid, more preferably a simple lipid, and further preferably a triacylglycerol.

The lipid obtained by the production method of the present invention can be utilized for food, as well as a plasticizer, an emulsifier incorporated into cosmetic products or the like, a cleansing agent such as a soap or a detergent, a fiber treatment agent, a hair conditioning agent, a disinfectant or an antiseptic.

With regard to the embodiments described above, the present invention also discloses methods of producing lipids, methods of modifying composition of fatty acids to be produced, transformants, methods of producing a transformant, proteins, genes, and recombinant vectors, described below.

<1> A method of producing lipids, containing the steps of:
culturing a transformant wherein the expression of a gene encoding any one of the following proteins (A) to (F) is enhanced, and
producing fatty acids or lipids containing these fatty acids as components:
(A) a protein consisting of the amino acid sequence set forth in SEQ ID NO: 2;
(B) a protein consisting of an amino acid sequence having 89% or more, preferably 90% or more, more preferably 92% or more, more preferably 93% or more, more preferably 94% or more, more preferably 95% or more, more preferably 96% or more, more preferably 97% or more, more preferably 98% or more, and further preferably 99% or more identity with the amino acid sequence of the protein (A), and having ACS activity;
(C) a protein consisting of the amino acid sequence set forth in SEQ ID NO: 4;
(D) a protein consisting of an amino acid sequence having 49% or more, preferably 50% or more, more preferably 55% or more, more preferably 60% or more, more preferably 65% or more, more preferably 70% or more, more preferably 75% or more, more preferably 80% or more, more preferably 85% or more, more preferably 90% or more, more preferably 92% or more, more preferably 93% or more, more preferably 94% or more, more preferably 95% or more, more preferably 96% or more, more preferably 97% or more, more preferably 98% or more, and further preferably 99% or more identity with the amino acid sequence of the protein (C), and having ACS activity;
(E) a protein consisting of the amino acid sequence set forth in SEQ ID NO: 6; and
(F) a protein consisting of an amino acid sequence having 85% or more, preferably 90% or more, more preferably 92% or more, more preferably 93% or more, more preferably 94% or more, more preferably 95% or more, more preferably 96% or more, more preferably 97% or more, more preferably 98% or more, and further preferably 99% or more identity with the amino acid sequence of the protein (E), and having ACS activity.

<2> A method of producing lipids, containing the steps of:
enhancing the expression of a gene encoding any one of the proteins (A) to (F) in a transformant, and
improving the productivity of medium-chain fatty acids or lipids containing these fatty acids as components, produced in a cell of the transformant.

<3> A method of modifying the composition of fatty acids, which containing enhancing the expressions of a gene encoding any one of the following proteins (A) to (F) in a transformant, to modify the composition of fatty acids or fatty acids of lipids containing these fatty acids as components produced in a cell of the transformant <4> The method described in the above item <3>, wherein the proportion of the medium-chain fatty acids in the whole fatty acids to be produced is increased.

<5> The method described in any one of the above items <1> to <4>, wherein the gene encoding any one of the proteins (A) to (F) is introduced into a host, to enhance the expression of the gene.

<6> A method of producing lipids, containing the steps of:
culturing a transformant into which a gene encoding any one of the proteins (A) to (F) is introduced, and
producing fatty acids or lipids containing these fatty acids as components.

<7> A method of producing lipids, containing the steps of:
culturing a transformant into which a gene encoding any one of the proteins (A) to (F) is introduced, and
improving productivity of medium-chain fatty acids or lipids containing these fatty acids as components to be produced.

<8> A method of modifying composition of fatty acids, containing the steps of:
culturing a transformant into which a gene encoding any one of the proteins (A) to (F) is introduced, and
modifying the composition of fatty acids or fatty acids of lipids containing these fatty acids as components to be produced.

<9> The method described in the above item <8>, wherein the proportion of the medium-chain fatty acids in the whole fatty acids to be produced is increased.

<10> The method described in any one of the above items <1> to <9>, wherein the protein (B) consists of an amino acid sequence in which 1 or several, preferably 1 or more and 71 or less, more preferably 1 or more and 64 or less, further preferably 1 or more and 51 or less, furthermore preferably 1 or more and 45 or less, furthermore preferably 1 or more and 38 or less, furthermore preferably 1 or more and 32 or less, furthermore preferably 1 or more and 25 or less, furthermore preferably 1 or more and 19 or less, furthermore preferably 1 or more and 12 or less, and furthermore preferably 1 or more and 6 or less amino acids, are deleted, substituted, inserted or added to the amino acid sequence of the protein (A).

<11> The method described in any one of the above items <1> to <9>, wherein the protein (D) consists of an amino acid sequence in which 1 or several, preferably 1 or more and 541 or less, more preferably 1 or more and 531 or less, further preferably 1 or more and 477 or less, furthermore preferably 1 or more and 424 or less, furthermore preferably 1 or more and 371 or less, furthermore preferably 1 or more and 318 or less, furthermore preferably 1 or more and 265 or less, furthermore preferably 1 or more and 212 or less, furthermore preferably 1 or more and 159 or less, furthermore preferably 1 or more and 106 or less, furthermore preferably 1 or more and 84 or less, furthermore preferably 1 or more and 74 or less, furthermore preferably 1 or more and 63 or less, furthermore preferably 1 or more and 53 or less, furthermore preferably 1 or more and 42 or less, furthermore preferably 1 or more and 31 or less, furthermore preferably 1 or more and 21 or less, and furthermore preferably 1 or more and 10 or less amino acids, are deleted, substituted, inserted or added to the amino acid sequence of the protein (C).

<12> The method described in any one of the above items <1> to <9>, wherein the protein (F) consists of an amino acid sequence in which 1 or several, preferably 1 or more and 112 or less, more preferably 1 or more and 74 or less, further preferably 1 or more and 59 or less, furthermore preferably 1 or more and 52 or less, furthermore preferably 1 or more and 44 or less, furthermore preferably 1 or more and 37 or less, furthermore preferably 1 or more and 29 or less, furthermore preferably 1 or more and 22 or less, furthermore preferably 1 or more and 14 or less, and furthermore preferably 1 or more and 7 or less amino acids, are deleted, substituted, inserted or added to the amino acid sequence of the protein (E).

<13> The method described in any one of the above items <1> to <12>, wherein the gene encoding any one of the proteins (A) to (F) is a gene consisting of any one of the following DNAs (a) to (f):
(a) a DNA consisting of the nucleotide sequence set forth in SEQ ID NO: 1;
(b) a DNA consisting of a nucleotide sequence having 70% or more, preferably 75% or more, more preferably 80% or more, further preferably 85% or more, furthermore preferably 90% or more, furthermore preferably 92% or more, furthermore preferably 93% or more, furthermore preferably 94% or more, furthermore preferably 95% or more, furthermore preferably 96% or more, furthermore preferably 97% or more, furthermore preferably 98% or more, and furthermore preferably 99% or more, identity with the nucleotide sequence of the DNA (a), and encoding the protein having ACS activity;
(c) a DNA consisting of the nucleotide sequence set forth in SEQ ID NO: 3;
(d) a DNA consisting of a nucleotide sequence having 70% or more, preferably 75% or more, more preferably 80% or more, further preferably 85% or more, furthermore preferably 90% or more, furthermore preferably 92% or more, furthermore preferably 93% or more, furthermore preferably 94% or more, furthermore preferably 95% or more, furthermore preferably 96% or more, furthermore preferably 97% or more, furthermore preferably 98% or more, and furthermore preferably 99% or more, identity with the nucleotide sequence of the DNA (c), and encoding the protein having ACS activity;

(e) a DNA consisting of the nucleotide sequence set forth in SEQ ID NO: 5;

(f) a DNA consisting of a nucleotide sequence having 70% or more, preferably 75% or more, more preferably 80% or more, further preferably 85% or more, furthermore preferably 90% or more, furthermore preferably 92% or more, furthermore preferably 93% or more, furthermore preferably 94% or more, furthermore preferably 95% or more, furthermore preferably 96% or more, furthermore preferably 97% or more, furthermore preferably 98% or more, and furthermore preferably 99% or more, identity with the nucleotide sequence of the DNA (e), and encoding the protein having ACS activity.

<14> The method described in the above item <13>, wherein the DNA (b) is a DNA consisting of a nucleotide sequence in which 1 or several, preferably 1 or more and 584 or less, more preferably 1 or more and 486 or less, further preferably 1 or more and 389 or less, furthermore preferably 1 or more and 292 or less, furthermore preferably 1 or more and 194 or less, furthermore preferably 1 or more and 155 or less, furthermore preferably 1 or more and 136 or less, furthermore preferably 1 or more and 116 or less, furthermore preferably 1 or more and 97 or less, furthermore preferably 1 or more and 77 or less, furthermore preferably 1 or more and 58 or less, furthermore preferably 1 or more and 38 or less, and furthermore preferably 1 or more and 19 or less nucleotides, are deleted, substituted, inserted or added to the nucleotide sequence of the DNA (a), and encoding the protein (A) or (B) having ACS activity, or a DNA capable of hybridizing with a DNA consisting of the nucleotide sequence complementary with the DNA (a) under a stringent condition, and encoding the protein (A) or (B) having ACS activity.

<15> The method described in the above item <13>, wherein the DNA (d) is a DNA consisting of a nucleotide sequence in which 1 or several, preferably 1 or more and 956 or less, more preferably 1 or more and 797 or less, further preferably 1 or more and 637 or less, furthermore preferably 1 or more and 478 or less, furthermore preferably 1 or more and 318 or less, furthermore preferably 1 or more and 255 or less, furthermore preferably 1 or more and 223 or less, furthermore preferably 1 or more and 191 or less, furthermore preferably 1 or more and 159 or less, furthermore preferably 1 or more and 127 or less, furthermore preferably 1 or more and 95 or less, furthermore preferably 1 or more and 63 or less, and furthermore preferably 1 or more and 31 or less nucleotides, are deleted, substituted, inserted or added to the nucleotide sequence of the DNA (c), and encoding the protein (C) or (D) having ACS activity, or a DNA capable of hybridizing with a DNA consisting of the nucleotide sequence complementary with the DNA (c) under a stringent condition, and encoding the protein (C) or (D) having ACS activity.

<16> The method described in the above item <13>, wherein the DNA (f) is a DNA consisting of a nucleotide sequence in which 1 or several, preferably 1 or more and 674 or less, more preferably 1 or more and 561 or less, further preferably 1 or more and 449 or less, furthermore preferably 1 or more and 337 or less, furthermore preferably 1 or more and 224 or less, furthermore preferably 1 or more and 179 or less, furthermore preferably 1 or more and 157 or less, furthermore preferably 1 or more and 134 or less, furthermore preferably 1 or more and 112 or less, furthermore preferably 1 or more and 89 or less, furthermore preferably 1 or more and 67 or less, furthermore preferably 1 or more and 44 or less, and furthermore preferably 1 or more and 22 or less nucleotides, are deleted, substituted, inserted or added to the nucleotide sequence of the DNA (e), and encoding the protein (E) or (F) having ACS activity, or a DNA capable of hybridizing with a DNA consisting of the nucleotide sequence complementary with the DNA (e) under a stringent condition, and encoding the protein (E) or (F) having ACS activity.

<17> The method described in any one of the above items <1> to <16>, wherein the proteins (A) to (F) are the ACS being capable of improving the content of medium-chain fatty acids in the living body.

<18> The method described in any one of the above items <1> to <17>, wherein expression of a gene encoding a TE is enhanced in the transformant.

<19> The method described in the above item <18>, wherein the TE is a TE having substrate specificity to a medium-chain acyl-ACP.

<20> The method described in the above item <18> or <19>, wherein the TE is a protein consisting of the amino acid sequence set forth in SEQ ID NO: 56, SEQ ID NO: 33, SEQ ID NO: 47, SEQ ID NO: 58, SEQ ID NO: 60, or SEQ ID NO: 62; or a protein consisting of an amino acid sequence having 50% or more (preferably 70% or more, more preferably 80% or more, and further preferably 90% or more) identity with the amino acid sequence of the protein, and having TE activity for a medium-chain acyl-ACP.

<21> The method described in any one of the above items <1> to <20>, wherein the transformant is a microorganism or a plant.

<22> The method described in the above item <21>, wherein the microorganism is a microalga.

<23> The method described in the above item <22>, wherein the microalga is an alga belonging to the genus *Nannochloropsis*, preferably *Nannochloropsis oculata*.

<24> The method described in the above item <21>, wherein the microorganism is *Escherichia coli*.

<25> The method described in the above item <21>, wherein the plant is *Arabidopsis thaliana*.

<26> The method described in any one of the above items <1> to <25>, wherein the lipids contain a medium-chain fatty acid or a fatty acid ester compound thereof, preferably a fatty acid having 6 or more and 14 or less carbon atoms or a fatty acid ester compound thereof, more preferably a fatty acid having 8 or more and 14 or less carbon atoms or a fatty acid ester compound thereof, more preferably a fatty acid having 10 or more and 14 or less carbon atoms or a fatty acid ester compound thereof, more preferably a fatty acid having 10, 12, or 14 carbon atoms or a fatty acid ester compound thereof, and more preferably a saturated fatty acid having 10, 12, or 14 carbon atoms (capric acid, lauric acid, or myristic acid) or a fatty acid ester compound thereof.

<27> The method described in any one of the above items <1> to <26>, wherein the transformant is cultured by using f/2 media.

<28> A transformant, wherein the expression of the gene encoding any one of the proteins (A) to (F) is enhanced in a host cell.

<29> A transformant, wherein the gene encoding any one of the proteins (A) to (F), or a recombinant vector containing the gene is introduced.

<30> A method of producing a transformant, wherein the gene encoding any one of the proteins (A) to (F) or a recombinant vector containing the gene is introduced.

<31> The transformant or the method of producing the same described in any one of the above items <28> to <30>, wherein the protein (B) is a protein specified in the above item <10>.

<32> The transformant or the method of producing the same described in any one of the above items <28> to <30>, wherein the protein (D) is a protein specified in the above item <11>.
<33> The transformant or the method of producing the same described in any one of the above items <28> to <30>, wherein the protein (F) is a protein specified in the above item <12>.
<34> The transformant or the method of producing the same described in any one of the above items <28> to <33>, wherein the gene encoding any one of the proteins (A) to (F) is a gene consisting of any one of the DNAs (a) to (f).
<35> The transformant or the method of producing the same described in the above item <34>, wherein the DNA (b) is a DNA specified in the above item <14>.
<36> The transformant or the method of producing the same described in the above item <34>, wherein the DNA (d) is a DNA specified in the above item <15>.
<37> The transformant or the method of producing the same described in the above item <34>, wherein the DNA (f) is a DNA specified in the above item <16>.
<38> The transformant or the method of producing the same described in any one of the above items <28> to <37>, wherein the proteins (A) to (F) are ACS being capable of improving the content of medium-chain fatty acids in the living body.
<39> The transformant or the method of producing the same described in any one of the above items <28> to <38>, wherein expression of a gene encoding a TE is enhanced.
<40> The transformant or the method of producing the same described in the above item <39>, wherein the TE is a TE having substrate specificity to a medium-chain acyl-ACP.
<41> The transformant or the method of producing the same described in the above item <39> or <40>, wherein the TE is a protein consisting of the amino acid sequence set forth in SEQ ID NO: 56, SEQ ID NO: 33, SEQ ID NO: 47, SEQ ID NO: 58, SEQ ID NO: 60, or SEQ ID NO: 62; or a protein consisting of an amino acid sequence having 50% or more (preferably 70% or more, more preferably 80% or more, and further preferably 90% or more) identity with the amino acid sequence of the protein, and having TE activity for a medium-chain acyl-ACP.
<42> The transformant or the method of producing the same described in any one of the above items <28> to <41>, wherein the transformant or the host is a microorganism or a plant.
<43> The transformant or the method of producing the same described in the above item <42>, wherein the microorganism is a microalga.
<44> The transformant or the method of producing the same described in the above item <43>, wherein the microalga is an alga belonging to the genus *Nannochloropsis*, preferably *Nannochloropsis oculata*.
<45> The transformant or the method of producing the same described in the above item <42>, wherein the microorganism is *Escherichia coli*.
<46> The transformant or the method of producing the same described in the above item <42>, wherein the plant is *Arabidopsis thaliana*.
<47> The proteins (A) to (F).
<48> The protein described in the above item <47>, wherein the protein (B) is a protein specified in the above item <10>.
<49> The protein described in the above item <47>, wherein the protein (D) is a protein specified in the above item <11>.
<50> The protein described in the above item <47>, wherein the protein (F) is a protein specified in the above item <12>.
<51> The protein described in any one of the above items <47> to <50>, wherein the proteins (A) to (F) are ACS being capable of improving the content of medium-chain fatty acids in the living body.
<52> A gene encoding the protein described in any one of the above items <47> to <51>.
<53> A gene encoding an acyl-CoA synthetase, consisting of any one of the DNAs (a) to (f).
<54> The gene described in the above item <53>, wherein the DNA (b) is a DNA specified in the above item <14>.
<55> The gene described in the above item <53>, wherein the DNA (d) is a DNA specified in the above item <15>.
<56> The gene described in the above item <53>, wherein the DNA (f) is a DNA specified in the above item <16>.
<57> A recombinant vector containing the gene described in any one of the above items <52> to <56>.
<58> Use of the transformant, a transformant obtained by the method of producing a transformant, the protein, the gene, or the recombinant vector described in any one of the above items <28> to <57>, for producing lipids.
<59> The use described in the above item <58>, wherein the lipids contain a medium-chain fatty acid or a fatty acid ester compound thereof, preferably a fatty acid having 6 or more and 14 or less carbon atoms or a fatty acid ester compound thereof, more preferably a fatty acid having 8 or more and 14 or less carbon atoms or a fatty acid ester compound thereof, more preferably a fatty acid having 10 or more and 14 or less carbon atoms or a fatty acid ester compound thereof, more preferably a fatty acid having 10, 12, or 14 carbon atoms or a fatty acid ester compound thereof, and more preferably a saturated fatty acid having 10, 12, or 14 carbon atoms (capric acid, lauric acid, or myristic acid) or a fatty acid ester compound thereof.

EXAMPLES

Hereinafter, the present invention will be described more in detail with reference to Examples, but the present invention is not limited thereto. Herein, the nucleotide sequences of the primers used in Examples are shown in Table 1.

TABLE 1

| Primer No. | Nucleotide sequence (5' → 3') | Primer Name |
|---|---|---|
| 9 | tcttttttgtgaagcatgattgaacaagatggatt | tub-neoF |
| 10 | tttcccccatcccgatcagaagaactcgtcaagaa | neo-hspR |
| 11 | cgagctcggtacccgactgcgcatggattgaccga | pUC-TUBpF |
| 12 | atatcaagaagctgtctttt | TuBpR |
| 13 | tcgggatgggggaaaaaaacctctg | Thsp-F |
| 14 | actctagaggatcccctttcgtaaataaatcagctc | pUC-Thsp-R |

TABLE 1-continued

| Primer No. | Nucleotide sequence (5' → 3') | Primer Name |
|---|---|---|
| 16 | gggatcctctagagtcgacctgcaggcatgcaagc | pUC19F |
| 17 | cgggtaccgagctcgaattc | pUC19R |
| 18 | tccgagcagattatgcccgcctacacgacga | VCPp-LACS2F |
| 19 | ctcttccacagaagcctacttgtagagattggcga | LACS2-VCPtR |
| 22 | cgagctcggtacccgggcggtcttttgtcctttcctc | pUC-VCP1F |
| 23 | aatctgctcggaggggaggatc | VCP1R |
| 24 | gcttctgtggaagagccagtg | VCP1tF |
| 25 | caatccatgcgcagtctgatcttgtccatctcgtg | VCP1t-TubR |
| 26 | actgcgcatggattgaccga | TubF |
| 28 | tccgagcagattatggccaagctgaccagcgc | ble-TubF |
| 29 | tttcccccatcccgattagtcctgctcctcggccac | ble-HSPtR |
| 30 | gcggccgctctagagtgcgagacggcccacgccgggac | NTEF |
| 31 | acaaaatattaacgcctagctaatatcaattttctttgg | NTER |
| 34 | tctagagcggccgcaccg | pBSR |
| 35 | gcgttaatattttgttaaaattcg | pBSF |
| 36 | ctggacaataccatgggatgggccttttcgccgccaag | NTE(VW)F |
| 37 | catggtattgtccagcaaag | NTE(VW)R |
| 39 | ccgcggtgttgcgcgctgcgagacggcccacgccg | VCP(TP)-NTEF |
| 40 | ctcttccacagaagcctagctaatatcaattttct | VCPt-NTER |
| 42 | ccctccgagcagattatgaagaccgccgctctcctc | VCPp-VCP(TP)F |
| 43 | gttctcccgcacccgcggtgttgcgcgc | VCP(TP)R |
| 44 | tccgagcagattatggcgctcttggccaggtg | VCP-LACS6F |
| 45 | ctcttccacagaagcttacatctcctctatttcca | LACS6-VCPR |
| 48 | cgcggtgttgcgcgctggaagccgaagccgaagct | BTE-VCP(TP)F |
| 49 | ctcttccacagaagcttacaccctcggttctgcgg | BTENCPtR |
| 50 | tccgagcagattatgggcaatacaccctccga | VCP-LACS11F |
| 51 | ctcttccacagaagctcatttgtacagagactcgatg | LACS11-VCPR |

Example 1 Production of a Transformant in which a LACS2 Gene and a TE Gene are Introduced into *Nannochloropsis oculata*, and Production of Lipids Using the Transformant (1) Construction of Plasmid for Neomycin Resistance Gene Expression A neomycin resistance gene (SEQ ID NO: 7), and a tubulin promoter sequence (SEQ ID NO: 8) derived from *Nannochloropsis gaditana* strain CCMP 526 described in a literature (Randor Radakovits, et al., Nature Communications, DOI:10.1038/ncomms1688, 2012) were artificially synthesized.

Using the thus-synthesized DNA fragments as templates, and a pair of the primer Nos. 9 and 10, and a pair of the primer Nos. 11 and 12 shown in Table 1, PCRs were carried out, to amplify the neomycin resistance gene and the tubulin promoter sequence, respectively.

*Nannochloropsis oculata* strain NIES-2145 was obtained from National Institute for Environmental Studies (NIES). *Nannochloropsis oculata* strain NIES-2145 was fully cultured in f/2 liquid medium (75 mg of $NaNO_3$, 6 mg of $NaH_2PO_4.2H_2O$, 0.5 μg of vitamin B12, 0.5 μg of biotin, 100 μg of thiamine, 10 mg of $Na_2SiO_3.9H_2O$, 4.4 mg of $Na_2EDTA.2H_2O$, 3.16 mg of $FeCl_3.6H_2O$, 12 μg of $FeCl_3.6H_2O$, 21 μg of $ZnSO_4.7H_2O$, 180 μg of $MnCl_2.4H_2O$, 7 μg of $CuSO_4.5H_2O$, 7 μg of $Na_2MoO_4.2H_2O$/artificial sea water 1 L), and then, the resultant was inoculated in 50 mL of f/2 medium so as to be 10% of the resultant in the f/2 medium, and cultured for six days at 25° C. under an atmosphere of 0.3% $CO_2$. After culturing, collected samples were crushed by using Multi-beads shocker, and then the genome DNA was prepared by phenol/chloroform treatment and ethanol precipitation. Using the thus-prepared genome as a template, and a pair of the primer Nos. 13 and 14 shown in Table 1, PCR was carried out to amplify the heat shock protein terminator sequence (SEQ ID NO: 15).

Furthermore, using a plasmid vector pUC19 (manufactured by Takara Bio) as a template, and a pair of the primer Nos. 16 and 17 shown in Table 1, PCR was carried out to amplify the plasmid vector pUC19.

These four amplified fragments were treated by restriction enzyme DpnI (manufactured by TOYOBO) respectively, and purified using a High Pure PCR Product Purification Kit (manufactured by Roche Applied Science). Then, obtained four fragments were fused using an In-Fusion HD Cloning Kit (manufactured by Clontech) to construct a plasmid for neomycin resistance gene expression.

Herein, the expression plasmid consisted of the pUC19 vector sequence and an insert sequence in which the tubulin promoter sequence, the neomycin resistance gene and the heat shock protein terminator sequence were linked in this order.

(2) Construction of Plasmid for LACS2 Gene Expression

The *Nannochloropsis oculata* strain NIES-2145 was cultured by a method in a manner similar to that described above. After culturing, collected samples were crushed by using Multi-beads shocker, and then RNA purification was conducted using RNeasy Plant Mini Kit (manufactured by Qiagen). The cDNA library was prepared by the thus-obtained total RNA, using SuperScript III First-Strand Synthesis System for RT-PCR (manufactured by invitrogen).

PCR using a pair of the primer Nos. 18 and 19 shown in Table 1 and the thus obtained cDNA as a template, was carried out to prepare a LACS2 gene fragment consisting of the nucleotide sequence set forth in SEQ ID NO: 1.

A VCP1 promoter sequence (SEQ ID NO: 20) and a VCP1 terminator sequence (SEQ ID NO: 21) were artificially synthesized based on the complete cds sequence (Accession number: JF957601.1) of the VCP1 (violaxanthin/(chlorophyll a)-binding protein) gene of *Nannochloropsis* sp. strain W2J3B registered in GenBank. Using the thus-synthesized DNA fragments as templates, and pairs of the primer Nos. 22 and 23, and the primer Nos. 24 and 25, shown in Table 1, PCRs were carried out to prepare the VCP1 promoter sequence and VCP1 terminator sequence, respectively.

Furthermore, using the above-described plasmid for neomycin resistance gene expression as a template, and a pair of the primer Nos. 26 and 17 shown in Table 1, PCR was carried out to amplify a fragment containing the cassette for neomycin resistance gene expression (the tubulin promoter sequence, the neomycin resistance gene, and the heat shock protein terminator sequence) and the pUC19 vector sequence.

These four fragments were fused by a method in a manner similar to that described above, to construct a plasmid for LACS2 gene expression.

Herein, the expression plasmid consisted of the pUC19 vector sequence and an insert sequence in which the VCP1 promoter sequence, the LACS2 gene, the VCP1 terminator sequence, the tubulin promoter sequence, the neomycin resistance gene and the heat shock protein terminator sequence were linked in this order.

(3) Construction of Plasmid for Zeocin Resistance Gene Expression

A zeocin resistance gene (SEQ ID NO: 27) was artificially synthesized. Using the thus-synthesized DNA fragments as a template, and a pair of the primer Nos. 28 and 29 shown in Table 1, PCR was carried out to amplify the zeocin resistance gene sequence.

Furthermore, using the above-described plasmid for neomycin resistance gene expression as a template, and a pair of the primer Nos. 12 and 13 shown in Table 1, PCR was carried out to amplify a DNA fragment containing the heat shock protein terminator sequence, the pUC19 vector sequence, and the tubulin promoter sequence.

Thus-obtained DNA fragments were fused by a method in a manner similar to the method described above, to construct a plasmid for zeocin resistance gene expression. Herein, the expression plasmid consisted of the pUC19 vector sequence and an insert sequence in which the tubulin promoter sequence, the zeocin resistance gene, and the heat shock protein terminator sequence were linked in this order.

(4) Construction of Plasmid for NoTE Gene Expression

Using the cDNA obtained from *Nannochloropsis oculata* strain NIES-2145 as a template, and a pair of the primer Nos. 30 and 31 shown in Table 1, PCR was carried out to prepare the NoTE gene fragments consisting of the nucleotide sequence of the 262nd to 864th positions set forth in SEQ ID NO: 32.

Further, using the plasmid vector of pBluescriptII SK(–) (manufactured by Stratagene) as a template, and a pair of the primer Nos. 34 and 35 shown in Table 1, PCR was carried out to amplify the pBluescriptII SK(–). Thus-amplified DNA fragments were treated by restriction enzyme DpnI (manufactured by TOYOBO).

These two fragments were fused by a method in a manner similar to the method described above, to construct a plasmid NoTE_262 for NoTE gene expression.

This plasmid NoTE_262 was constructed by removing amino acid residues of the 1st to 87th positions on an N-terminal side of the amino acid sequence (SEQ ID NO: 38) encoded in NoTE gene, and fusing, to the upstream of the removed terminus, amino acid residues of the 1st to 29th positions on an N-terminal side of a LacZ protein derived from the plasmid vector pBluescriptII SK(–). In the following plasmid notation, "NoTE_262" means that a plasmid had the nucleotide sequence of the 262nd to 864th positions set forth in SEQ ID NO: 32 as a nucleotide sequence encoding a polypeptide consisting of the amino acid sequence of the 88th to 287th positions set forth in SEQ ID NO: 33.

(5) Construction of Plasmid for Modified NoTE Gene Expression

PCR was carried out by using the plasmid for NoTE gene expression, NoTE_262, as a template, and a pair of the primer Nos. 36 and 37 shown in Table 1, to obtain gene fragments (SEQ ID NO: 38) in which a part of nucleotides of the 262nd to 864th positions of the nucleotide sequence set forth in SEQ ID NO: 32 was subjected to mutation. Herein, the nucleotide sequence set forth in SEQ ID NO: 38 is the nucleotide sequence wherein a codon encoding the valine of the 204th position of the amino acid sequence set forth in SEQ ID NO: 33 was substituted with a codon encoding tryptophan (TGG).

The plasmids for modified NoTE expression NoTE_262 (V204W), was constructed by using the gene fragment according to a method in a manner similar to that described above. PCR was carried out by using the thus-constructed plasmid for modified NoTE expression, NoTE_262 (V204W), as a template, and a pair of the primer Nos. 39 and 40 shown in Table 1, to obtain modified NoTE gene fragment consisting of the nucleotide sequence set forth in SEQ ID NO: 38.

A VCP1 chloroplast transit signal sequence (SEQ ID NO: 41) was artificially synthesized based on the complete cds sequence of the VCP1 gene of *Nannochloropsis* sp. strain W2J3B registered in GenBank. Using the thus-synthesized DNA fragments as a template, and a pair of the primer Nos. 42 and 43 shown in Table 1, PCR was carried out, to prepare the VCP1 chloroplast transit signal sequence.

Further, using the VCP1 promoter sequence and VCP1 terminator sequence, which were artificially synthesized in a manner similar to that described above, as templates, and a pair of the primer Nos. 22 and 23, and a pair of the primer Nos. 24 and 25 shown in Table 1, PCRs were carried out, to obtain the VCP1 promoter sequence, and VCP1 terminator sequence, respectively.

Furthermore, using the above-described plasmid for zeocin resistance gene expression as a template, and a pair of the primer Nos. 26 and 17 shown in Table 1, PCR was carried out to amplify a DNA fragment containing the tubulin promoter sequence, the zeocin resistance gene, the heat shock protein terminator sequence, and the pUC19 vector sequence.

The obtained gene fragments were fused by a method in a manner similar to that described above, to construct a plasmid for modified NoTE gene expression.

Herein, the expression plasmid consisted of the pUC19 vector sequence and an insert sequence in which the VCP1 promoter sequence, the VCP1 chloroplast transit signal sequence, the modified NoTE gene fragment, the VCP1 terminator sequence, the tubulin promoter sequence, the zeocin resistance gene, and the heat shock protein terminator sequence were linked in this order.

(6) Introduction of a LACS2 Gene and a Modified NoTE Gene into *Nannochloropsis oculata*

Using the above-described plasmid for modified NoTE gene expression as a template, and a pair of the primer Nos. 22 and 14 shown in Table 1, PCR was carried out to amplify the fragment for modified NoTE gene expression (a DNA fragment consisted of the VCP1 promoter sequence, the VCP1 chloroplast transit signal sequence, the modified NoTE gene, the VCP1 terminator sequence, the tubulin promoter sequence, the zeocin resistance gene, and the heat shock protein terminator sequence).

The amplified gene fragment was purified using High Pure PCR Product Purification Kit (manufactured by Roche Applied Science). Herein, sterilized water was used for elution upon purification without using an elution buffer included in the kit.

About $1 \times 10^9$ cells of *Nannochloropsis oculata* strain NIES-2145 were washed with 384 mM sorbitol solution to completely remove a salt, and the resultant was used as a host cell for transformation. The fragment for modified NoTE gene expression was mixed by about 500 ng with the host cell, and electroporation was carried out under the conditions of 50 µF, 500Ω and 2,200 v/2 mm.

After 24 hours recovery cultivation in f/2 liquid medium, the resultant was inoculated in f/2 agar medium containing 2 µg/mL of zeocin, and cultured for two to three weeks under 12 h/12 h light-dark conditions at 25° C. under an atmosphere of 0.3% $CO_2$. Obtained colonies were selected as the transgenic strain (hereinafter, referred to as "NoTE strain").

Using the above-described plasmid for LACS2 gene expression as a template, and a pair of the primer Nos. 22 and 14 shown in Table 1, PCR was carried out to amplify the fragment for LACS2 gene expression (a DNA fragment containing the VCP1 promoter sequence, the LACS2 gene, the VCP1 terminator sequence, the tubulin promoter sequence, the neomycin resistance gene, and the heat shock protein terminator sequence). The DNA fragment was introduced into the modified NoTE gene transgenic strain according to the method in a manner similar to that described above. Then, obtained colonies cultured in neomycin-containing medium were selected as the modified NoTE gene and LACS2 genes transgenic strain (hereinafter, referred to as "NoTE+LACS2 strain").

(7) Production of Fatty Acids Using the Transformant

The selected strain by the method described above was inoculated to 50 mL of medium in which a nitrogen concentration in the f/2 medium was reinforced 15 times, and a phosphorus concentration therein was reinforced 5 times (hereinafter, referred to as "N15P5 medium"), and subjected to shaking culture for four weeks under the 12 h/12 h light-dark conditions at 25° C. under the atmosphere of 0.3% $CO_2$, to prepare preculture fluid.

Then, 10 mL of the preculture fluid was inoculated to 40 mL of the N15P5 medium, and subjected to shaking culture under the 12 h/12 h light-dark conditions at 25° C. under the atmosphere of 0.3% $CO_2$.

After three weeks cultivation, lipid components contained in the culture fluid were analyzed by the method described below.

(8) Extraction of Lipids and Analysis of Fatty Acids Contained Therein

To 1 mL of the culture fluid, 50 µL of 1 mg/mL 7-pentadecanone as an internal standard was added, and then 0.5 mL of chloroform, 1 mL of methanol and 10 µL of 2N hydrochloric acid were further added. The mixture was vigorously stirred and then was left for 30 minutes. Further, 0.5 mL of chloroform and 0.5 mL of 1.5% KCl were added thereto. The mixture was stirred and centrifuged for 15 minutes at 3,000 rpm, and then the chloroform layer (lower layer) was collected with Pasteur pipette.

A nitrogen gas was blown onto the resultant chloroform layer to be dried into solid. Then, 0.7 mL of 0.5 N potassium hydroxide/methanol solution was added to the sample, and the mixture was kept warm at 80° C. for 30 minutes. Next, 1 mL of 14% boron trifluoride solution (manufactured by Sigma-Aldrich) was added to the sample, and the mixture was kept warm at 80° C. for 10 minutes. Thereafter, 1 mL of hexane and 1 mL of saturated saline were added thereto, and the mixture was vigorously stirred and then was left for 30 minutes at room temperature. Then, the hexane layer being upper layer was collected to obtain fatty acid methyl esters.

Under the measuring conditions as follows, the obtained fatty acid methyl esters were provided for gas chromatographic analysis.

<Gas Chromatography Conditions>
Analysis Instruments: 7890A (Agilent technology)
Capillary column: DB-1 MS (30 m×200 µm×0.25 µm, manufactured by J & W Scientific)
Mobile phase: high purity helium
Flow rate in column: 1.0 mL/minute
Elevated temperature program: 100° C. (1 minute)→10° C./minute→300° C. (5 minutes)
Equilibrating time: 1 minute
Injection port: split injection (split ratio: 100:1), pressure: 14.49 psi, 104 mL/minute
Amount of injection: 1 µL
Cleaning vial: methanol/chloroform
Detector temperature: 300° C.

Moreover, the fatty acid methyl esters were identified by providing the identical sample under identical conditions described above.

Amounts of the fatty acid methyl esters of each of the fatty acids were quantitatively determined based on the peak areas of waveform data obtained by the above gas chromatographic analysis. The peak area corresponding to each of the fatty acid methyl esters was compared with that of 7-pentadecanone as the internal standard, and carried out corrections between the samples, and then the amount of each of the fatty acids per liter of the culture fluid was calculated. Further, the total amount of the fatty acids was calculated by summing the amounts of each of the fatty acids thus obtained, and proportion of each of the fatty acids in the total amount of the fatty acids was calculated.

Table 2 shows the results. Herein, in Table below, "FA" presents total amount of fatty acids, and "Fatty Acid Composition (% FA)" presents a proportion of a weight of each fatty acid relative to a weight of the total fatty acid (%). Further, "n" designates an integer of 0 to 5. For example, when "C18:n" is described, the description means a total of each fatty acid having compositions of C18:0, C18:1, C18:2, C18:3, C18:4 and C18:5.

TABLE 2

| | Fatty Acid Composition (% FA) | | | | | | | (n = 3) FA (mg/L) |
|---|---|---|---|---|---|---|---|---|
| | C10:0 | C12:0 | C14:0 | C16:1 | C16:0 | C18:n | C20:n | |
| NoTE | 3.32 ± 0.11 | 9.79 ± 0.40 | 14.72 ± 0.12 | 26.98 ± 0.39 | 10.77 ± 0.36 | 14.56 ± 0.49 | 19.85 ± 1.63 | 1165.36 ± 248.97 |
| NoTE + LACS2 | 6.55 ± 0.51 | 12.48 ± 0.42 | 15.85 ± 0.34 | 23.74 ± 0.49 | 8.33 ± 0.26 | 13.68 ± 0.91 | 19.37 ± 0.93 | 1448.84 ± 77.13 |

As shown in Table 2, a significant change in the fatty acid composition was able to be confirmed by introducing the LACS2 gene thereinto. Specifically, proportions of long-chain fatty acids such as C16:1 (palmitoleic acid), C16:0 (palmitic acid) and C18:n were significantly reduced in the NoTE+LACS2 strain in comparison with the NoTE strain. Then, proportions of medium-chain fatty acids (C10:0 (capric acid), C12:0 (lauric acid) and C14:0 (myristic acid)) markedly increased. Further, the total amount of fatty acids also increased in the NoTE+LACS2 strain in comparison with the NoTE strain.

From the results described above, it became apparent that the LACS2 gene can be preferably used in improving productivity of the medium-chain fatty acids.

Example 2 Production of a Transformant in which a LACS6 Gene and a BTE Gene are Introduced into *Nannochloropsis oculata*, and Production of Fatty Acids Using the Transformant (1) Construction of Plasmid for LACS6 Gene Expression Using the cDNA library of *Nannochloropsis oculata* strain NIES-2145 prepared in Example 1 as a template, and a pair of the primer Nos. 44 and 45 shown in Table 1, PCR was carried out to prepare the LACS6 gene fragments consisting of the nucleotide sequence set forth in SEQ ID NO: 3.

Further, the plasmid for LACS2 gene expression constructed in Example 1 as a template, and a pair of the primer Nos. 23 and 24 shown in Table 1, PCR was carried out to amplify a gene fragment consisted of the VCP1 promoter sequence, the VCP1 terminator sequence, the cassette for neomycin resistance gene expression (the tubulin promoter sequence, the neomycin resistance gene, and the heat shock protein terminator sequence), and the pUC19 vector sequence.

These two fragments were fused by a method in a manner similar to that described in Example 1, to construct a plasmid for LACS6 gene expression. Herein, the expression plasmid consisted of the pUC19 vector sequence and an insert sequence in which the VCP1 promoter sequence, the LACS6 gene, the VCP1 terminator sequence, the tubulin promoter sequence, the neomycin resistance gene and the heat shock protein terminator sequence were linked in this order.

(2) Construction of Plasmid for BTE Gene Expression

The nucleotide sequence (SEQ ID NO: 46) encoding the BTE which is described in WO 92/20236 was artificially synthesized. Using the thus-synthesized DNA fragment as a template, and a pair of the primer Nos. 48 and 49 shown in Table 1, PCR was carried out, to prepare the BTE gene fragment. Note that, in the DNA fragment, the segment corresponding to the chloroplast transit signal (85 amino acids of the N-terminal) of BTE consisting of the amino acid sequence set forth in SEQ ID NO: 47 was deleted.

Furthermore, using the plasmid for NOTE gene expression constructed in Example 1 as a template, and a pair of the primer Nos. 24 and 43 shown in Table 1, PCR was carried out to amplify a DNA fragment containing the VCP1 promoter sequence, the VCP1 chloroplast transit signal sequence, the VCP1 terminator sequence, the tubulin promoter sequence, the zeocin resistance gene, the heat shock protein terminator sequence, and the pUC19 vector sequence.

The obtained gene fragments were fused by a method in a manner similar to that described above, to construct a plasmid for BTE gene expression.

(3) Introduction of a LACS6 Gene and a BTE Gene into *Nannochloropsis oculata*

Using the above-described plasmid for BTE gene expression as a template, and a pair of the primer Nos. 22 and 14 shown in Table 1, PCR was carried out to amplify the fragment for BTE gene expression (a DNA fragment containing the VCP1 promoter sequence, the BTE gene, the VCP1 terminator sequence, the tubulin promoter sequence, the zeocin resistance gene, and the heat shock protein terminator sequence).

This gene fragment was introduced into *Nannochloropsis oculata* strain NIES-2145 according to the same method as in Example 1. Then the BTE gene transgenic strain (hereinafter, referred to as "BTE strain") was selected.

Using the above-described plasmid for LACS6 gene expression as a template, and a pair of the primer Nos. 22 and 14 shown in Table 1, PCR was carried out to amplify the fragment for LACS6 gene expression (a DNA fragment containing the VCP1 promoter sequence, the LACS6 gene, the VCP1 terminator sequence, the tubulin promoter sequence, the neomycin resistance gene, and the heat shock protein terminator sequence).

This gene fragment was introduced into the BTE gene transgenic strain according to the same method as in Example 1. Then the obtained colonies in neomycin-containing medium were selected as the BTE gene and LACS6 gene transgenic strain (hereinafter, referred to as "BTE+LACS6 strain").

(4) Production of Fatty Acids Using the Transformant and Extraction of Lipids and Analysis of Fatty Acids Contained Therein A transformant obtained by the above-described method was cultured in the same manner as in Example 1, extraction of lipids was performed, and analysis of fatty acids contained therein was performed. Table 3 shows the results.

TABLE 3

| | Fatty Acid Composition (% FA) | | | | | | (n = 3) FA |
|---|---|---|---|---|---|---|---|
| | C12:0 | C14:0 | C16:1 | C16:0 | C18:n | C20:n | (mg/L) |
| BTE | 4.84 ± 0.49 | 4.98 ± 0.62 | 28.44 ± 2.62 | 29.97 ± 2.39 | 16.13 ± 1.37 | 15.65 ± 3.26 | 1837.32 ± 234.12 |
| BTE + LACS6 | 7.69 ± 0.20 | 5.47 ± 0.16 | 27.28 ± 1.75 | 27.62 ± 0.60 | 15.93 ± 0.65 | 16.00 ± 1.05 | 1760.22 ± 244.18 |

As shown in Table 3, a significant change in the fatty acid composition was able to be confirmed by introducing the LACS6 gene thereinto. Specifically, a proportion of a long-chain fatty acid such as C16:1 (palmitoleic acid), C16:0 (palmitic acid) and C18:n were significantly reduced in the BTE+LACS6 strain in comparison with the BTE strain. Then, proportions of medium-chain fatty acid (C12:0 (lauric acid) and C14:0 (myristic acid)) markedly increased.

From the results described above, it became apparent that the LACS6 gene can be preferably used in improving productivity of the medium-chain fatty acids.

Example 3 Production of a Transformant in which a LACS11 Gene and a TE Gene are Introduced into *Nannochloropsis oculata*, and Production of Fatty Acids Using the Transformant (1) Construction of Plasmid for LACS11 Gene Expression Using the cDNA library of *Nannochloropsis oculata* strain NIES-2145 prepared in Example 1 as a template, and a pair of the primer Nos. 50 and 51 shown in Table 1, PCR was carried out to prepare the LACS11 gene fragments consisting of the nucleotide sequence set forth in SEQ ID NO: 5.

Further, using the plasmid for LACS2 gene expression constructed in Example 1 as a template, and a pair of the primer Nos. 23 and 24 shown in Table 1, PCR was carried out to amplify a gene fragment consisted of the VCP1 promoter sequence, the VCP1 terminator sequence, the cassette for neomycin resistance gene expression (the tubulin promoter sequence, the neomycin resistance gene, and the heat shock protein terminator sequence), and the pUC19 vector sequence.

These two fragments were fused by a method in a manner similar to that described in Example 1, to construct a plasmid for LACS11 gene expression. Herein, the expression plasmid consisted of the pUC19 vector sequence and an insert sequence in which the VCP1 promoter sequence, the LACS11 gene, the VCP1 terminator sequence, the tubulin promoter sequence, the neomycin resistance gene and the heat shock protein terminator sequence were linked in this order.

(2) Introduction of a LACS11 Gene and a Modified NoTE Gene into *Nannochloropsis oculata*

Using the above-described plasmid for LACS11 gene expression as a template, and a pair of the primer Nos. 22 and 14 shown in Table 1, PCR was carried out to amplify the fragment for LACS11 gene expression (a DNA fragment containing the VCP1 promoter sequence, the LACS11 gene, the VCP1 terminator sequence, the tubulin promoter sequence, the neomycin resistance gene, and the heat shock protein terminator sequence).

This gene fragment was introduced into NoTE strain prepared in Example 1 according to the same method as in Example 1. Then the obtained colonies in neomycin-containing medium were selected as the NoTE gene and LACS11 gene transgenic strain (hereinafter, referred to as "NoTE+LACS11 strain").

(3) Production of Fatty Acids Using the Transformant and Extraction of Lipids and Analysis of Fatty Acids Contained Therein A transformant obtained by the above-described method was cultured in the same manner as in Example 1, extraction of lipids was performed, and analysis of fatty acids contained therein was performed. Table 4 shows the results.

TABLE 4

| | Fatty Acid Composition (% FA) | | | | | | | (n = 3) FA |
|---|---|---|---|---|---|---|---|---|
| | C10:0 | C12:0 | C14:0 | C16:1 | C16:0 | C18:n | C20:n | (mg/L) |
| NoTE | 1.58 ± 0.41 | 8.38 ± 1.29 | 15.92 ± 0.97 | 27.23 ± 1.01 | 13.80 ± 2.36 | 14.94 ± 0.51 | 18.15 ± 1.11 | 638.13 ± 77.39 |
| NoTE + LACS11 | 3.89 ± 0.04 | 16.00 ± 0.18 | 20.88 ± 0.10 | 20.65 ± 0.48 | 10.05 ± 0.52 | 11.85 ± 0.22 | 16.67 ± 0.79 | 713.69 ± 96.93 |

As shown in Table 4, a significant change in the fatty acid composition was able to be confirmed by introducing the LACS11 gene thereinto. Specifically, proportions of long-chain fatty acids such as C16:1 (palmitoleic acid), C16:0 (palmitic acid) and C18:n were significantly reduced in the NoTE+LACS11 strain in comparison with the NoTE strain. Then, proportions of medium-chain fatty acids (C10:0 (capric acid), C12:0 (lauric acid) and C14:0 (myristic acid)) markedly increased. Further, the total amount of fatty acids also increased in the NoTE+LACS11 strain in comparison with the NoTE strain.

From the results described above, it became apparent that the LACS11 gene can be preferably used in improving productivity of the medium-chain fatty acids.

As described above, the transformant in which productivities of the medium-chain fatty acids are improved can be prepared by enhancing the expression of the LACS gene as specified in the present invention. Further, productivity of the medium-chain fatty acids can be improved by culturing this transformant.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2016-084680 filed in Japan on Apr. 20, 2016, which is entirely herein incorporated by reference.

What is claimed is:

1. A method of producing lipids, comprising the steps of: culturing a microalga transformant in which expression of a gene encoding any one of the following acyl-CoA synthetase proteins (A) to (F) and also expression of a gene encoding an acyl-ACP thioesterase has been enhanced, and
producing medium-chain fatty acids or lipids containing these fatty acids as components:
(A) a protein consisting of the amino acid sequence set forth in SEQ ID NO: 2;
(B) a protein consisting of an amino acid sequence having 90% or more sequence identity with the amino acid sequence of protein (A), and having acyl-CoA synthetase activity;
(C) a protein consisting of the amino acid sequence set forth in SEQ ID NO: 4;
(D) a protein consisting of an amino acid sequence having 90% or more sequence identity with the amino acid sequence of protein (C), and having acyl-CoA synthetase activity;
(E) a protein consisting of the amino acid sequence set forth in SEQ ID NO: 6; and
(F) a protein consisting of an amino acid sequence having 90% or more sequence identity with the amino acid sequence of protein (E), and having acyl-CoA synthetase activity;
wherein the gene encoding the acyl-CoA synthetase has been introduced into the transformant, and
wherein culturing the transformant produces more medium-chain fatty acids or lipids containing the medium-chain fatty acids as components than does a cell that is the same as the transformant except that it has not been transformed with the gene encoding the acyl-CoA synthetase.

2. The method according to claim 1, wherein both the gene encoding any one of proteins (A) to (F) and the gene encoding the acyl-ACP thioesterase have been introduced into the transformant, and expression of both genes is enhanced in the transformant.

3. The method according to claim 1, wherein the acyl-ACP thioesterase is a protein consisting of the amino acid sequence set forth in SEQ ID NO: 56, SEQ ID NO: 33, SEQ ID NO: 47, SEQ ID NO: 58, SEQ ID NO: 60, or SEQ ID NO: 62.

4. The method according to claim 1, wherein the microalga transformant belongs to the genus *Nannochloropsis*.

5. The method according to claim 4, wherein the microalga transformant belongs to the species *Nannochloropsis oculata*.

6. The method according to claim 1, wherein the lipid contains a fatty acid having 6 or more and 14 or less carbon atoms or a fatty acid ester compound thereof.

7. The method according to claim 1, wherein the acyl-ACP thioesterase is a protein consisting of an amino acid sequence that has 90% or more sequence identity with the amino acid sequence set forth in SEQ ID NO: 56, SEQ ID NO: 33, SEQ ID NO: 47, SEQ ID NO: 58, SEQ ID NO: 60, or SEQ ID NO: 62, and has acyl-ACP thioesterase activity for a medium-chain acyl-ACP.

* * * * *